(12) United States Patent
Rosen et al.

(10) Patent No.: US 6,868,287 B1
(45) Date of Patent: Mar. 15, 2005

(54) CARDIAC REMODELING

(75) Inventors: Michael R. Rosen, New York, NY (US); Nicholas S. Peters, London (GB); Yoram Palti, Haifa (IL)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/505,458

(22) Filed: Feb. 11, 2000

Related U.S. Application Data

(60) Provisional application No. 60/119,896, filed on Feb. 12, 1999.

(51) Int. Cl.[7] ............................................. A61N 1/362
(52) U.S. Cl. ........................................................ 607/9
(58) Field of Search ............................. 607/4, 5, 9, 14, 607/25, 129, 130, 132

(56) References Cited

U.S. PATENT DOCUMENTS

| | | | |
|---|---|---|---|
| 3,937,226 A | | 2/1976 | Funke |
| 4,088,140 A | | 5/1978 | Rockland et al. |
| 4,628,937 A | | 12/1986 | Hess et al. |
| 4,787,389 A | | 11/1988 | Tarjan |
| 5,111,811 A | * | 5/1992 | Smits ........................ 128/419 |
| 5,174,289 A | | 12/1992 | Cohen |
| 5,203,348 A | * | 4/1993 | Dahl et al. ................. 128/784 |
| 5,243,978 A | | 9/1993 | Duffin |
| 5,366,485 A | * | 11/1994 | Kroll et al. .................... 607/5 |
| 5,681,308 A | * | 10/1997 | Edwards et al. ............. 606/41 |
| 5,800,464 A | | 9/1998 | Kieval |
| 5,814,079 A | * | 9/1998 | Kieval ............................ 607/4 |
| 5,824,028 A | * | 10/1998 | Knisley ...................... 607/119 |
| 5,871,505 A | * | 2/1999 | Adams et al. .................. 607/5 |
| 5,873,896 A | * | 2/1999 | Ideker ........................... 607/14 |
| 5,947,899 A | * | 9/1999 | Winslow et al. ............ 600/410 |
| 6,152,882 A | * | 11/2000 | Prutchi ....................... 600/509 |
| 6,363,279 B1 | * | 3/2002 | Ben-Haim et al. ............. 607/9 |

OTHER PUBLICATIONS

Katz AM: T wave "Memory": Possible causal relationship to stress–induced changes in cardiac ion channels? J Cardiovasc Electrophysiol 1992;3:150–159.

Page, E. Cardiac Gap Junctions. In: *The Heart and Cardiovascular System*. H.A. Fozzard, E. Haber, R.B. Jennings, A.M. Katz, and H.E. Morgan (eds) . New York: Raven Press Ltd. 1992; 1003–1048. (Exhibit 2).

Spach MS, Miller WT III, Dolber PC, Kootsey JM, Sommer JR, Mosher CE Jr. The functional role of structural complexities in the propagation of depolarization in the atrium of the dog. Cardiac conduction distrubances due to discontinuities of effective axial resistivity. *Circ Res.* 1982; 50:175–191. (Exhibit 3).

Smith JH, Green CR, Peters NS, Rothery S, Severs NJ. Altered patterns of gap junctions distribution in ischemic heart disease. An immunohistochemical study of human myocardium using laser scanning confocal microscopy. *Am J Pathol.* 1991; 139:801–821. (Exhibit 4).

(List continued on next page.)

*Primary Examiner*—Jeffrey R. Jastrzab
*Assistant Examiner*—Frances P. Oropeza
(74) *Attorney, Agent, or Firm*—John P. White; Cooper & Dunham LLP

(57) ABSTRACT

The invention provides a method of treating a heart to remodel gap junctions, obtain gap junctional remodeling and/or alteration or effective refractory period comprising contacting linked multiple electrode pairs to an epicardial surface of a heart, and connecting the electrode pairs to a pacemaker to apply periodic electrical signals to the epicardial surface through the electrode pairs, the signals being applied for a sufficient time and having characteristics sufficient to remodel gap junctions, obtain gap junctional remodeling and/or alteration of effective refractory period in the heart. The invention also provides a device comprising a strip of electrode material having mounted thereon linked multiple electrode pairs arranged in two columns.

60 Claims, 12 Drawing Sheets

OTHER PUBLICATIONS

Luke RA, Saffitz JE. Remodeling of ventricular conduction pathways in healed canine infarct border zones. *J Clin Invest*. 1991;87:1594–1602. (Exhibit 5).

Peters NS, Green CR, Poole–Wilson PA, Severs NJ. Reduced content of connexin43 gap junctions in ventricular myocardium from hypertrophied and ischaemic human hearts. *Circulation*. 1993;88:864–875. (Exhibit 6).

Campos De Carvalho AC, Tanowitz HB, Wittner M. Dermietzel R, Roy C, Hertzberg EL, Spray DC. Gap junction distribution is altered between cardiac myocytes infected with Trypanosoma cruzi. *Circ Res*. 1992;70:733–742. (Exhibit 7).

Bastide B, Neyses L, Ganten D, Paul M, Willecke K, Traub O. Gap junction protein connexin40 is preferentially expressed in vascular endothelium and conductive bundles of rat myocardium and is increased under hypertensive conditions. *Circ Res*. 1993;73:1138–1149. (Exhibit 8).

Fast VG, Darrow BJ, Saffitz JE, Kleber AG. Anisotropic activation spread in heart cell monolayers assessed by high–resolution optical mapping. Role of tissue discontinuities. *Circ Res*. 1996;79:115–127. (Exhibit 9).

Guerrero–P–A; Schuessler–R–B; Davis–L–M; Beyer–E–C; Johnson–C–M; Yamada–K–A; Saffits–J–E: Slow ventricular conduction in mice heterozygous fora connexin43 null mutation. Journal of Clinical Investigation 1997;99(8): 1991–1998 (Exhibit 10).

Peters NS, Severs NJ, Coromilas J, Wit AL. Disturbed connexin43 gap junctional distribution correlates with the location of reentrant circuits in the epicardial border zone of healing canine infarcts that cause ventricular tachycardia. *Circulation*. 1997 95;988–996 (Exhibit 11).

Wijffels MCEF, Kirchhof CJHJ, Dorland R, Allessie MA: Atrial fibrillation begets atrial fibrillation. Circulation 1995;92: 1954–1968. (Exhibit 12).

Kajstura–J; Zhang–X; Liu–Y; Szoke–E; Cheng–W; Olivetti–G; Hintze–T–H; Anversa–P: The cellular basis of pacing–induced dilated cardiomyopathy: Myocyte cell loss and myocyte cellular reactive hypertrophy. Circulation 1995; 92(8) : 2306–2317 (Exhibit 13).

Rosenbaum MB, Blanco HH, Elizari MV, Lazzari JO, Davidenko JM: Electronic modulation of the T wave and cardia memory. Am J Cartel 1982;50:2130222. (Exhibit 14).

Chatteree K, Harris A, Davies G, Leatham A: Electrocardiographic changes subsequent to artificial ventricular depolarization. Br Heart J 1969;31:770–779 (Exhibit 15).

Shvilkin A, Danilo P, Jr. Wang J, Burkhoff D, Anyukhovsky EP, Sosunov EA, Hara M. Rosen MR. The evolution and resolution of long–term cardiac memory. Circulation 1998;97:1810–1817. (Exhibit 16).

del Balzo U, Rosen MR: T wave changes persisting after ventricular pacing in canine heart are altered by 4–aminopyridine but not by lidocaine. Circulation 1992;85: 1464–1472. (Exhibit 17).

Tan, RC; Joyner, RW: Electronic influences on action potentials from isolated ventricular cells. Circ Res: 1990:67: 1071–1081) (Exhibit 18).

Yu H, McKinnon D, Dixon JE, Gao J, Wymore R, Cohen IS, Danilo, P Jr., Shvilkin A, Anyukhovsky EP, Sosunov EA, Hara M, Rosen MR: The transient outward current, $I_{to}$, is altered in cardiac memory. Circulation, 1999; 88:1898–1905. (Exhibit 19).

Anyukhovsky EP, Sosunov EA, Feinmark SJ, et al: Effects of quinidine on repolarization in canine epicardium, midmyocardium, and endocardium: II. In vivo study. Circulation 1997;96:4019–4026. (Exhibit 20).

Anyukhovsky EP. Sosunov EA, Gainullin RZ, Rosen MR. The controversial M cell J Cardiovasc Electrophysiol, *in press*. (Exhibit 21).

Yeh–H–I; Dupont–E; Coppen–S; Rothery–S; Severs–N–J: Gap junction localization and connexin expression in cytochemically identified endothelial cells of arterial tissue. Journal of Histochemistry and Cytochemistry 1997; 45(4) : 539–550 (Exhibit 22).

Hoyt RH, Cohen ML, Saffitz JE. Distribution and three–dimensional structure of intercellular junctions in canine myocardium. Circ. Res. 1989;64:563–574. (Exhibit 23).

Peters NS, Wit AL. Myocardial architecture and ventricular arrhythmogenesis. Circulation 1997;97: 1746–1754. (Exhibit 24).

Spach MS, Dolber PC. The relation between discontinuous propagation in anisotropic cardiac muscle and the "vulnerable period" of reentry. In: *Cardiac Electrophysiology and Arrhythmias* D.P. Zipes and J. Jalife (eds). Grune and Stratton, Orlando. 1985;241–252. (Exhibit 25).

Wit AL, Janse MJ: Basic mechanisms of arrhythmias, in *The Ventricular Arryhythmisa of Ischemia and Infarction*. New York, Futura, 1992, pp. 1–160. (Exhibit 26).

Lesh MD, Pring M, Spear JF: Cellular uncoupling can unmask dispersion of action potential duration in ventricular myocardium. Circ. Res. 1989;65:1426–1440. (Exhibit 27).

Elvan A. Wylie K, Zipes DP: Pacing–induced chronic atrial fibrillation impairs sinus node function in dogs. Electrophysiological remodeling. Circulation 1996;94:2953–60. (Exhibit 28).

Yue–L; Feng–J; Gaspo–R; Li–G–R; Wang–Z; Nattel–S: Ionic remodeling underlying action potential changes in a canine model of atrial fibrillation. Circulation Research 1997;81(4) : 512–525. (Exhibit 29).

Quan W, Rudy Y: unidirectional block and reentry of cardiac excitation: a model study. Circ. Res. 1990;66:367–382. (Exhibit 30).

Van–Der–Velden–Huub–M–W; Van–Kempen–Marjan–J–A; Wijffels–Maurits–C–E–F; Van–Zijverden–Maaike; Groenewegen–W–Antoinette; Allessie–Maurits–A; Jongsma–Habo–J: Altered pattern of connexin40 distribution in persistent atrial fibrillation in the goat. Journal–of–Cardiovascular–Electrophysiology. Jun., 1998;9(6) 595–607. (Exhibit 31).

Patel P, Jones DG, Hadjinicolou L, Glenville B, Stanbridge R, Severs NJ, Peters NS. Changes in human atrial connexin expression in atrial fibrillation and ischemic heart disease. Circulation 1997;96(8) :I–17. (Exhibit 32).

\* cited by examiner

Pacing-Induced T Wave Changes On ECG In the Canine Heart

Pacing-Induced T Wave Changes On VCG In the Canine Heart
Frontal Plane

A. Sinus rhythm - Control    D. Sinus rhythm - Memory

B. Ventricular pacing

C. T wave progression crosshair size = 0.5 x 0.5 mV

CARDIAC REMODELING

CROSS REFERENCE TO RELATED APPLICATIONS

This application is based on U.S. Provisional Application No. 60/119,896, filed Feb. 12, 1999, and is incorporated by reference herein.

FIELD OF THE INVENTION

This application is directed to cardiac remodeling. More particularly, this application is directed to pacing of the epicardium or endocardium to induce cardiac electrical, mechanical, ion channel and gap junctional remodeling.

BACKGROUND OF THE INVENTION

Within this application several publications are references by arabic numerals within parentheses. Full citations for these and other references may be found at the end of the specification immediately preceding the claims. The disclosures of all of these publication in their entireties are hereby incorporated by reference into this application in order to more fully describe the state of the art to which this invention pertains.

Arrhythmias of the heart, such as fibrillation, are well known to those familiar with the heart. Localized or diffuse lesions of the myocardium, which may result from any one of various reasons, often lead to a pronounced dispersion of repolarization and refractoriness. As a result, under certain circumstances the heart does not experience a normal sequential depolarization but, rather, there results an abnormal activation pattern and/or dispersion of repolarization. An abnormal impulse occurring during this period can lead to electrical fragmentation, and consequent initiation of ventricular fibrillation.

It is known that the proper application of an electrical shock to the heart can change a fibrillating heart back to synchronous action of all myocardial fibers; that is, the heart can be defibrillated. Defibrillation induced by electrical shock of the heart results in a regular development of propagation of electrical excitation by means of simultaneous depolarization of all myocardial fibers that have gone out of step to cause the arrhythmia. Many defibrillation devices are known in the prior art for providing a defibrillation pulse after the arrhythmia has commenced.

However, it has become apparent that electrical defibrillation is not an ideal means of therapy for arrhythmia problems. First of all, it is not immediately available in most cases, and even where implantable defibrillation devices are used, they provide stimulation signals only after the dangerous condition of arrhythmia already exists. Further, though implantable defibrillators were developed to eliminate existing ventricular fibrillation as rapidly as possible, they can do so only after detection of the actual state of fibrillation; and because of the high power requirements of the electrical shocks required to defibrillate, the operating time of such implantable defibrillators is highly limited. Further, even after detecting the advent of fibrillation, such prior art defibrillators require a discreet period of charge time before providing a defibrillation shock.

The determinants of myocardial conduction and repolarization include the dimensions and packing geometry of the myocytes, and the properties of the gap junction which are the membrane specializations that form the low resistance pathways for the flow of intercellular current. (1, 2) Changes in quantity and distribution of gap junctions and their constituent proteins, connexins, have been demonstrated in various disease states (3–7) and experimental data indicate that such changes may cause heterogeneous slowing of conduction (8, 9) and are strongly implicated in reentry (10). There is also increasing evidence for the general concept of tachyarrhythmia-induced, and of pacing-induced, electrophysiological remodeling of myocardium. (11, 12) Pacing-induced alterations in activation pathways cause changes in the T wave that long outlast the return to sinus rhythm (13–16), and are generally referred to as "cardiac memory" (13, 17). Given that low resistance connections between cells are the basis for electrotonus, and that electronic current flow modulates the voltage-time course of repolarization of nearby myocytes (18), remodeling of gap-junctional coupling may be implicated in the mechanism of cardiac memory. Changes in conduction and repolarization that occur in circumstances of altered activation may be critical to the pathophysiology of arrhythmias, and both would be facilitated by altered electrotonus that might accompany gap junctional remodeling.

SUMMARY OF THE INVENTION

It is an object of the invention to provide an apparatus and method for cardiac remodeling.

It is also an object of the invention to provide an apparatus and method for pacing of the epicardium or endocardium to induce cardiac electrical, mechanical, ion channel and gap junctional remodeling.

It is a further object of the invention to provide an apparatus and method for long-term, multi-point stimulation of as well as multi-point recording from a functioning heart.

It is a yet further object of the invention to provide an apparatus and method for pacing of the heart for sustained periods of time to induce remodeling of gap junctions and ion channels, to sustain an antiarrhythmic effect and alter contractile patterns as well.

One aspect of the invention provides a method of treating a heart to remodel gap junctions, comprising contacting linked multiple electrode pairs to an epicardial surface of a heart, and connecting the electrode pairs to a pacemaker to apply periodic electrical signals to the epicardial surface through said electrode pairs, said signals being applied for a sufficient time and having characteristics sufficient to remodel gap junctions in the heart.

According to another aspect of the invention, a device is provided for treating a heart to obtain gap junctional remodeling, comprising a substrate having linked multiple electrode pairs for contacting an epicardial surface of a heart and for delivering periodic pacemaker electrical signals to the epicardial surface through said electrode pairs, to remodel gap junctions in the heart.

Another aspect of the invention is a method of treating a heart to alter the effective refractory period, comprising contacting linked multiple electrode pairs to an epicardial surface of a heart, and connecting the electrode pairs to a pacemaker to apply electrical signals to the epicardial surface, said signals being applied for a sufficient time and having characteristics sufficient to alter the effective refractory period of the heart.

Another aspect of the invention provides a device for treating a heart to alter the effective refractory period, comprising a substrate having linked multiple electrode pairs for contacting an epicardial surface of a heart and for delivering periodic pacemaker electrical signals to the epicardial surface through said electrode pairs, to alter the effective refractory period in the heart.

According to another aspect of the invention, a method is provided for treating a heart to induce ion channel remodeling, comprising contacting linked multiple electrode pairs to an epicardial surface of a heart, and connecting the electrode pairs to a pacemaker to apply periodic electrical signals to the epicardial surface, said signals being applied for a sufficient time and having characteristics sufficient to induce ion channel remodeling in the heart.

Yet another aspect of the invention provides a device for treating a heart to induce ion channel remodeling, comprising a substrate having linked multiple electrode pairs for contacting an epicardial surface of a heart and for delivering periodic pacemaker electrical signals to the epicardial surface through said electrode pairs, to induce ion channel remodeling in the heart.

These and other objects of the invention will become more apparent from the accompanying figures, following detailed description and attached claims.

DETAILED DESCRIPTION OF THE INVENTION

Figure 1:
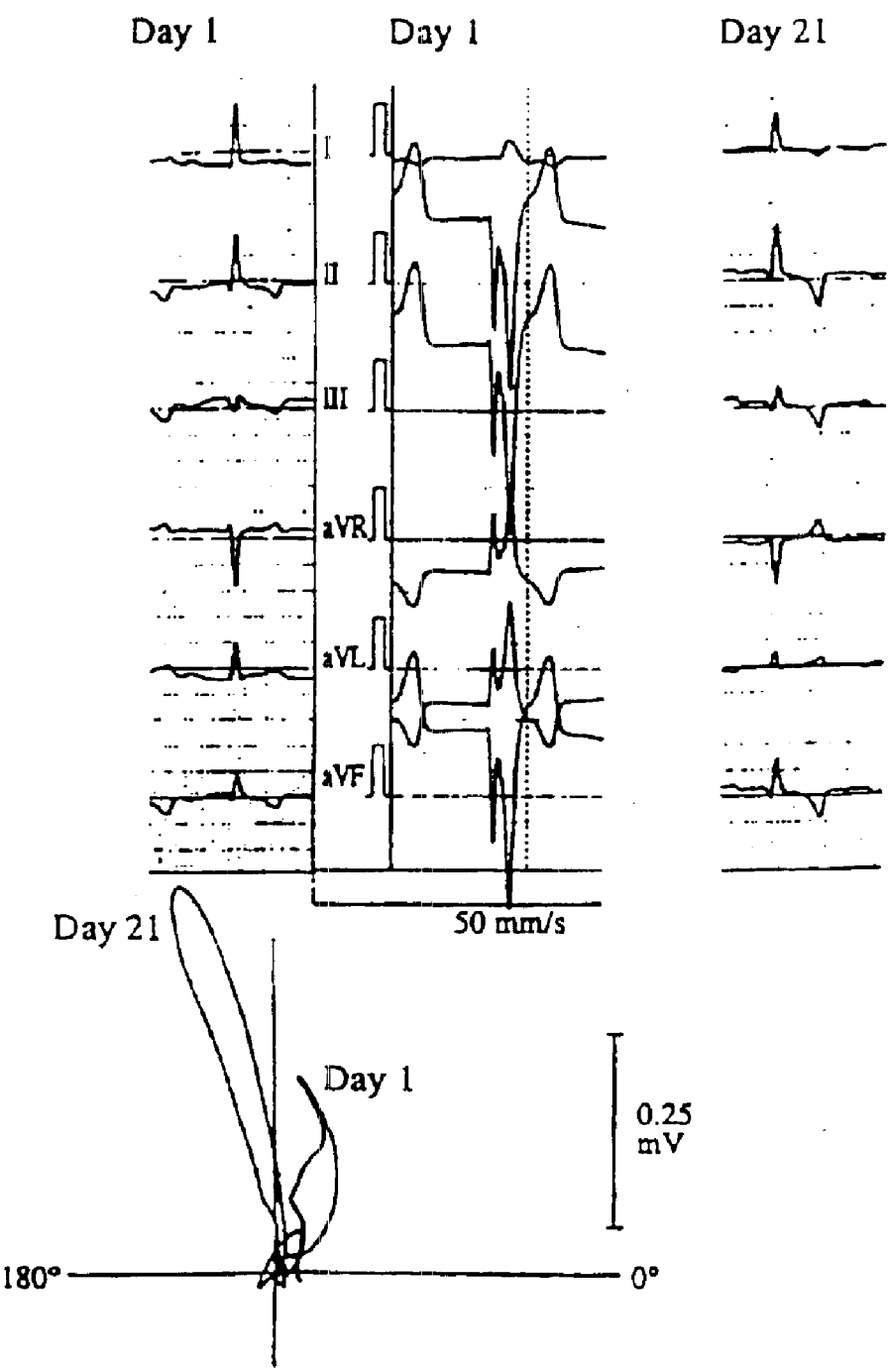
FIG. 1 is a six lead electrocardiogram and frontal plane T wave vectrocardiogram of a dog.

The invention provides a method of treating a heart to remodel gap junctions, comprising contacting linked multiple electrode pairs to an epicardial surface of a heart, and connecting the electrode pairs to a pacemaker to apply periodic electrical signals to the epicardial surface through said electrode pairs, said signals being applied for a sufficient time and having characteristics sufficient to remodel gap junctions in the heart.

The step of contacting may comprise contacting a strip electrode material having linked multiple electrode pairs mounted thereon.

The strip electrode material may comprise a strip of medical grade polyurethane, wherein the strip is about 7 cm×1 cm in dimension.

The linked multiple electrode pairs may be arranged in two columns with one electrode in each pair in one column, and the other electrode in each pair in the other column. Preferably, each electrode in the electrode pair is about 2 mm from each other, and wherein each electrode pair is about 5 mm from its closest electrode pair.

The electrodes may comprise platinum, and may even consist essentially of unalloyed platinum.

The step of contacting may comprise sewing a substrate strip containing linked multiple electrode pairs to an epicardial surface of the heart. The step of contacting may comprise locating a transvenous catheter containing linked multiple electrode pairs into an epicardial vein. The step of contacting may comprise placing electrodes into heart ventricles for endocardial activation.

The invention also provides a device for treating a heart to obtain gap junctional remodeling, comprising a substrate having linked multiple electrode pairs for contacting an epicardial surface of a heart and for delivering periodic pacemaker electrical signals to the epicardial surface through said electrode pairs, to remodel gap junctions in the heart.

The substrate may comprise a strip of electrode material having mounted thereon the linked multiple electrode pairs. The electrode material may comprise medical grade polyurethane.

The electrode pairs may be arranged in two columns with one electrode in each pair in one column, and the other electrode in each pair in the other column. Preferably one electrode in the pair is about 2 mm from the other electrode in the pair, and each electrode pair is about 5 mm from its closest electrode pair.

The electrodes are preferably comprised of platinum, and more preferably consist essentially of unalloyed platinum. Each electrode is preferably connected to an insulated stainless steel wire.

According to another aspect of the invention, a method of treating a heart to alter the effective refractory period is provided, comprising contacting linked multiple electrode pairs to an epicardial surface of a heart, and connecting the electrode pairs to a pacemaker to apply electrical signals to the epicardial surface, said signals being applied for a sufficient time and having characteristics sufficient to alter the effective refractory period of the heart.

Another aspect of the invention provides a device for treating a heart to alter the effective refractory period, comprising a substrate having linked multiple electrode pairs for contacting an epicardial surface of a heart and for delivering periodic pacemaker electrical signals to the epicardial surface through said electrode pairs, to alter the effective refractory period in the heart.

A yet further aspect of the invention provides a method of treating a heart to induce ion channel remodeling, comprising contacting linked multiple electrode pairs to an epicardial surface of a heart, and connecting the electrode pairs to a pacemaker to apply periodic electrical signals to the epicardial surface, said signals being applied for a sufficient time and having characteristics sufficient to induce ion channel remodeling in the heart.

The invention also provides a device for treating a heart to induce ion channel remodeling, comprising a substrate having linked multiple electrode pairs for contacting an epicardial surface of a heart and for delivering periodic pacemaker electrical signals to the epicardial surface through said electrode pairs, to induce ion channel remodeling in the heart.

Propagation of the action potential from cell to cell is dependent on a number of architectural characteristics of the myocardium. (24) These architectural determinants of myocardial conduction include the dimensions and packing geometry of the constituent myocytes, the number of cells with which each cell makes contact (typically about 10 in the normal mammalian ventricle (23, 5)), and the distribution of the gap junctions which are the membrane specializations that form the low resistance pathway for the flow of intercellular current (1). As a principal determinant of myocardial conduction, alteration in the organization of gap-junctional coupling affects conduction and is directly implicated in promoting reentrant arrhythmogenesis. (25, 10, 26, 27)

There is increasing experimental evidence for the role of changes in both the action potential (11) and in the functional morphology of myocardial architecture in reentrant arrhythmogenesis. (25, 10, 24) What has recently become apparent, however, is that electrophysiological remodeling may not only have a causative role in reentrant arrhythmogenesis, but may also be a direct consequence of tachyarrhythmia, and that this remodeling may act to perpetuate the arrhythmic tendency (11). This phenomenon has been demonstrated in the atria of animal models of both atrial fibrillation (11) and very high rate atrial pacing (28, 29), coining the phrase "atrial fibrillation begets atrial fibrillation" (11). As an explanation for this self-perpetuating tachyarrhythmia-induced atrial remodeling, it has been suggested that whatever the initial trigger for the tachyarrhythmia, the resultant remodeling is caused by the rapid stimulation of the atrial myocardium and constitutes part of a tachycardia-induced myopathic process.

The results of our experimental studies of the ventricle show that altering the pattern of myocardial activation causes a remodeling of its myocardial gap-junctional organization. Importantly, as the pacing was at low rate, this finding cannot be attributed to a tachycardia-induced myopathy. Furthermore, we have previously reported microsphere, hemodynamic and cell capacitance studies in this model which exclude myocardial ischemia, hypertrophy or congestive ventricular failure as having a causative role (15, 19). The remodeling of Cx43 gap junctions occurred differentially in different layers and different regions of the LV wall, being most evident in the epicardial layer near the pacing site.

That alteration of the ventricular activation sequence causes changes in myocardial electrophysiological function is well documented, and one clinical manifestation of this is cardiac memory, in which the T-wave of the ECG during sinus rhythm assumes a vector approaching that of the paced or arrhythmic QRS complex (13, 14, 17). This phenomenon has been extensively investigated in the paced ventricles in this canine model, and results from changes in the action potential that occur differentially between the endo-, mid-, and epimyocardial layers of the left ventricular wall (15). These changes in the action potential results from changes in a subset of ion channels (19), and require new protein synthesis (15). The results of the present study indicate that alterations in the action potentials of the individual cells may be determined in part by the way they are electrically coupled. Alterations in coupling may therefore play a role in the genesis of cardiac memory not only by causing localized differential modulation of patterns and velocities of depolarizing wave fronts, but by altering electro tonic current flow during repolarization. Computer modeling studies indicate that the progressive uncoupling of cardiac myocytes reduces electro tonic current flow, thereby unmasking the intrinsic differences in action potential characteristics that exist among neighboring cells, layers of the ventricular wall, and differences in action potential characteristics that exist among neighboring cells, layers of the ventricular wall, and different regions of the ventricle, thus altering the normal heterogeneity (27, 28). That heterogeneity of repolarization across myocardial layers is, in fact, altered in the setting of cardiac memory has been demonstrated by us previously (15).

Of importance in elucidating the potential physiological consequences of the altered connexin43 gap-junctional organization are the subtle, yet consistent and significant changes in activation that occur with the induction of pacing-induced cardiac memory. First, during ventricular pacing, activation was not altered to the LV sites that were relatively near to the pacing electrode and were activated earliest, but was slowed to the RV site that was the latest activated. And second, during atrial pacing, activation was not altered to the sites activated earliest, but now was delayed to the last-activated site, the LV base. In other words, in both settings the site to which conduction was slowest during control manifested the delay in activation. One possible cause of the change in activation is the remodeling of gap-junctional organization that occurred in these animals.

Such localized gap-junctional remodeling may not only facilitate the changes seen in the conduction and repolarization of the normal cardiac impulse, but has important implications for understanding reentrant arrhythmias. Changes in gap-junctional organization have been demonstrated in the fibrillating mammalian atrium (31, 32), and we have shown that a specific pattern of gap-junctional disorganization appears to define the inducibility and location of the reentrant circuit in the epicardial border zone of the model of healing canine infarct (10). The results of the present study raise the possibility that gap-junctional remodeling may be a consequence of the abnormal activation pattern during the arrhythmia. Further, these findings raise the intriguing possibility that abnormal conduction pathways even during sinus rhythm, caused by regional structural and functional changes I the diseased myocardium, such as the presence of an infarct, may produce localized remodeling of gap-junctional coupling which may be central to the development of the arrhythmogenic substrate. In other words, just as has been shown for the atrium that "fibrillation begets fibrillation," there is a structural basis for proposing that alterations in the activation pattern of ventricular myocardium cause changes in the distribution of the architectural determinants of myocardial conduction, thereby perpetuating arrhythmogenesis.

An aspect of the present invention concerns providing an apparatus and method to enable long-term, multi-point stimulation of as well as multi-point recording from a functioning heart. In other words, the system has to include multiple electrical contact points of suitable properties that can be used to stimulate the heart muscle by passing current, or record its electric activity by measuring potential differences, positioned such that they make firm and stable contact at selected points on the internal or external surface of a heart i.e., contracting and moving heart. These contact points are to be connected via flexible insulated leads to the stimulating current or potential recording units. All of this has to form a two-dimensional array of high density circuitry.

Two basically different technologies are currently in wide use for the fabrication of electrical conducting leads and contact points: silicon chip —microelectronics technology (called hereafter "Chip") and printed circuit technology (called hereafter "Prints"). The first is in wide use in construction of practically all types of modern electronic micro-chips, such as microprocessors, while the second is mainly used as a base for connecting between the various electric components (conductors, resistors, capacitors, etc.) and electronic active elements (transistors, processors, etc.)

From the points of view relevant to the present invention the main characteristics and differences between the two technologies are as follows:

Chip construction is based around silicon which has the mechanical properties of glass and therefore has mechanical limitations: it is not flexible and if thin tends to break easily. In contrast, Prints construction is based around plastics such as polyimid which are very flexible and do not break when in the form of thin films.

The cutting of the base material to individual units is done by etching in Chips and laser beams in Prints. This makes the process more expensive for Prints.

The standard Chip technology allows for smaller and more dense circuitry; however, the limitation of about 5 microns in Prints technology does not pose a problem for our purposes.

Presently only Chip technology allows the integration of active elements in the circuitry.

In order to satisfy the above requirements and in view of the above characteristics of the two technologies, the optimal choice would be use of the flexible Prints. The Prints can be made of two thin electrically-insulating and biocompatible plastic material sheets glued together so as to be holding in between them conductive metal strips that are sandwiched to form a compound flexible sheet, about 0.03–0.3 mm in thickness. One such preferred embodiment would be two polyimid sheets which are very strong, biocompatible and to which living cells tend to adhere well. The conducting metal strips can be made from any metal used in such circuits. For example, aluminum, provided that their exposed sections are coated with a suitable conducting element such as gold, platinum, etc. Such plating is also standard in the industry. The contact points are made by perforating the plastic at the desired locations. Such exposure of the metal is made, for example, by laser beams. The exposed areas are to serve as heart muscle contacts as well as to form suitable connectors to the electronic activating units.

The overall geometry of the circuit and contacts is practically unlimited and is usually made by means of masks generated by computer programs and lithography and implicated on sheets of stationary paper sizes. The sheets can be cut into practically any shapes by laser beams.

In principle, Chip technology can allow the building of circuits which practically contain such a thin layer of silicone so as to be flexible. There may be other Chip technologies that would make the Chip sufficiently flexible. Such circuits would have the advantage that they can contain active elements on board, for example, the first amplification stage.

TESTING

Electrical Instrumentation of Canine Model

Mongrel dogs of either sex weighing 22 to 27 kg were anaesthetized with propofol 6 mg/kg IV, followed by inhalation of isoflurane 92%). Under sterile conditions, the chest was opened and the heart suspended in a pericardial cradle. Two groups of dogs were prepared.

In Group I (7 dogs), a Medtronic permanent pacing lead (model 6917) was attached to the epicardium of the anterolateral left ventricle. The lead was connected to a Medtronic MINIX 8340 pulse generator that was placed in a subcutaneous pocket. No other leads were attached to minimize manipulation and instrumentation of the hearts for subsequent histological examination (see below).

In Group II (5 dogs) preparation was as above, but different instrumentation was performed. Here, the Medtronic pacemaker was implanted into the posterobasal left ventricular epicardium, and bipolar surface electrodes were sewn to the epicardium in the following regions: right atrial appendage, left ventricular posterior wall 2 cm away from the pacemaker, anterior base, and right ventricular free wall. In this way we could pace atrium or ventricle and perform measurements of cardiac activation during ventricular or atrial pacing. Because of the additional instrumentation, these animals were used for studies of cardiac activation and repolarization, only, and not for studies involving histology and immunohistochemistry.

In both groups, the incisions were closed, and the animals were allowed to recover for 2 to 3 weeks, during which time they were trained to lie quietly on the right side for the performance of ECG recordings. Ventricular pacing was then instituted (mode VVO, rate 110 to 120 bpm; amplitude, 3.3 to 5V; pulse width, 0.35 to 0.05 mg) at a rate 10% to 15% higher than each animal's sinus rate for 3 weeks. Twenty-four-hour monitoring on random days confirmed reliable capture for at east 75% of the time.

Cardiac hemodynamics, myocardial blood flow and ventricular myocyte capacitance (indicating cell size) have been shown previously to be unaffected by the pacing in this model (15, 19). Five unoperated dogs in sinus rhythm maintained under identical conditions acted as controls. ECGs were recorded at baseline and at 2–3 day intervals during the 3-week study period, with the animals resting quietly on the right side.

Ventricular activation and repolarization were studied as follows: in addition to recording cardiac frontal plane vectors, as previously described (15), activation times were measured as the interval between the stimulus artifact (during ventricular pacing) or the onset of the QRS complex (during atrial pacing) to the maximum deflection of the first derivative of the local electrogram. Activation-recovery intervals were measured from the steepest deflection of the local electrogram to the maximum peak of the first derivative of the terminal limb of the T wave (20, 21).

Tissue Handling

After 3 weeks of ventricular pacing, final ECGs were recorded from Group I animals during atrial pacing and ventricular pacing. These dogs were anaesthetized with pentobarbital, 30 mg/kg, IV, and the heart removed and weighed. Transmural LV samples were excised from the anterior left ventricular wall, 1 to 2 cm from the pacing site, and from the posterior LV wall, distant from the pacing site. All specimens were divided into epimyocardial (epi), midmyocardial (mid) and endomyocardial (endo) layers, and immediately snap frozen in liquid nitrogen.

Connexin Immunohistochemistry

Frozen sectioning of the samples was carried out in a cryostat at −20° C., producing 10 $\mu$m tissue sections of random orientation, which were picked up on slides coated with poly-L-lysine, stored at −20° C., and fixed in methanol for 5 minutes at −20° C. Standard histological staining and light microscopy was carried out on all tissue samples to confirm preservation, cell structure and orientation, and for photography. Connexin immunohistochemistry was carried out on epi-, mid-, and endomyocardial layers.

The antibody used for the localization of cardiac gap-junctional connexin43 was $IgG_1$, raised in mice against a synthetic peptide corresponding to positions 252–270 of the native connexin43 from rat (Chemicon International Inc.). For connexin40 labeling, a rabbit anti-rat antibody (against amino acid residues 254–268) was used as both unpurified serum and in a purified form. Further details regarding this antibody kindly supplied by Professor Nicholas J. Severs of Imperial College, London can be found elsewhere (22).

The fluorochrome Cy3 (peak absorption wavelength 550 nm, peak emission wavelength 570 nm) was used for these studies, conjugated to antibodies (Chemicon International Inc.) raised against immunoglobulin from mouse (for connexin43 labeling) and rabbit (for connexin40 labeling) as appropriate.

Immunolabelling Protocol

Following fixation and blocking slides were incubated first with the primary connexin antibody, and then with the appropriate Cy3-conjugated secondary antibody. For Connexin43 Immunolabelling, the primary antibody was used at a dilution of 1:1000, with 1% BSA, for 1 hour at room temperature. For Connexin40 Immunolabelling, a range of conditions was used, leading to the conclusion that no detectable connexin40 labeling was expressed in either the control or paced canine ventricular myocytes (see Results below).

Image Acquisition and Analysis

Immunolabelled sections were examined using a Leica TCS 4D laser scanning confocal microscope running on SCANware software with the digitized images stored on 250 Mb magneto-optical disks.

Connexin43 Western Blotting

Total tissue homogenates were prepared from the frozen tissue samples to give a solution of final concentration 0.5 µg/µl in sample buffer. 3.0 µg of total protein from each sample were resolved by polyacrylamide gel electrophoresis (BioRad) on a 12.5% gel (with a 4.5% stacker). The gel was run at 60V until the dye front was through the stacker and then at 150V. The gel was electrophoretically transferred onto a polyvinylidene fluoride membrane at constant voltage 30V. Transfer was assessed by Ponceau S (Sigma). The membrane was blocked in the dilution buffer (TBS/0.2% Tween20 (Merck)/1% blot qualified BSA) for 30 minutes, followed by incubation with the primary antibody for connexin43 (as used for immunohistochemistry, above), diluted 1:1000 in dilution buffer for one hour. After washing, the membrane was incubated with the secondary alkaline phosphates conjugated anti-mouse antibody (Pierce), diluted 1:2500 with dilution buffer, for one hour. After washing, the membrane was incubated with alkaline phosphate buffer (0.1 M Tris pH 9.5, 0.1 M $MgCl_2$) for 5 minutes, followed by incubation with freshly prepared substrate solution (Promega Corporation). Following densitometric quantification of band intensity, all values were corrected for protein loading using the actin band on a coomassie stained gel run in parallel.

Statistical Analysis

For studies of cardiac activation, the time for propagation of an impulse to the various sites on the ventricle was recorded using the QS on the body surface ECG as a reference point. Data were analyzed using repeated measures ANOVA, with Bonferroni's test applied where the f value so permitted. The results of Western connexin quantification of the sample groups were compared by unpaired, two-tailed t-tests, and the ECG QRS duration for each animal compared by paired t-test. In all studies p-values of <0.05 were considered significant.

RESULTS

Evolution of Electrophysiological Changes

FIG. 1 is a six lead electrocardiogram and frontal plane T wave vectrocardiogram of one dog on day 1 during atrial pacing just before, and then shortly after, initiating ventricular pacing, and on day 21, one hour after the return to atrial pacing. By day 21 the T wave during atrial pacing has tracked the paced QRS complex. ECG calibrations =1 mV and 50 mm/sec. The vector calibration =0.5 mV.

FIG. 1 is a representative experiment from a Group II dog, demonstrating the ECG and the frontal plane T wave vector during atrial pacing and one hour after initiating ventricular pacing on day 1, and during atrial pacing an hour after the end of 21 days of ventricular pacing. The evolution of the atrially-paced T wave and its vector are such that at 21 days it has tracked the ventricularly-paced QRS complex. The characteristics of the ECG and of cardiac T wave vectors for Group I and II animals are shown in Table 1. No significant changes occurred in the heart rate, P—R interval, QRS duration or QT interval in either group, as has been previously described (15). Also, as previously described, there are significant changes in the T wave vector, which, as demonstrated in FIG. 1, assumes an angle and amplitude that track those of the paced QRS complex.

Of critical importance, however, is the changes that occurred in the ventricularly paced QRS duration. In both groups this increased significantly (Table 1). Hence, both Group I animals that had been paced from the anterior left ventricle and used for subsequent study of connexins and the Group II animals that had been paced from the posterior left ventricle and instrumented for the study of electrograms showed complementary changes in the T wave and its vector and comparable prolongation of the paced QRS complex over the 21 days of pacing. QRS prolongation was not apparent when activation was via the AV node during sinus rhythm (Group I) or atrial pacing (Group II), as indicated in the following Table 1.

TABLE 1

Electrocardiographic characteristics of Group I (paced from anterior LV) and Group II (paced from posterior LV) dogs on days 0 and 21 of the study. Group I animals were in sinus rhythm and Group II were atrially paced at the time of the measurements.

|  | P-R (ms) | QRS (ms) | QRS during Ventricular Pacing+ (ms) | QT (ms) | HR (min − 1) | Tvect angle (day 0) ΔT angle (day 21) | T vect amp (mV) | T vect displacement |
|---|---|---|---|---|---|---|---|---|
| Group I | | | | | | | | |
| Day 0 | 130 ± 5.1 | 54 ± 1.5 | 109 ± 2.7 | 231 ± 4.4 | 99 ± 2.5 | −63 ± 21.2 | .37 ± .06 | 0 |
| Day 21 | 127 ± 3.9 | 56 ± 0.6 | 113 ± 1.7* | 226 ± 2.7 | 90 ± 3.7 | 43 ± 3.7* | .89 ± .05* | .89 ± .07* |

TABLE 1-continued

Electrocardiographic characteristics of Group I (paced from anterior LV) and Group II (paced from posterior LV) dogs on days 0 and 21 of the study. Group I animals were in sinus rhythm and Group II were atrially paced at the time of the measurements.

| | P-R (ms) | QRS (ms) | QRS during Ventricular Pacing[+] (ms) | QT (ms) | HR (min − 1) | Tvect angle (day 0) ΔT angle (day 21) | T vect amp (mV) | T vect displacement |
|---|---|---|---|---|---|---|---|---|
| Group II | | | | | | | | |
| Day 0 | 170 ± 7.9 | 59 ± 3.3 | 109 ± 5.2 | 208 ± 3.5 | 120 | −116 ± 13.3 | 1.00 ± 0.2 | 0 |
| Day 21 | 166 ± 6.2 | 60 ± 3.5 | 113 ± 5.3* | 210 ± 4.3 | 120 | 20 ± 6.0* | 1.57 ± 0.2* | .73 ± .07* |

*p < 0.05 compared Day 0
[+]Only these measurements were made during ventricular pacing.

Figure 2:
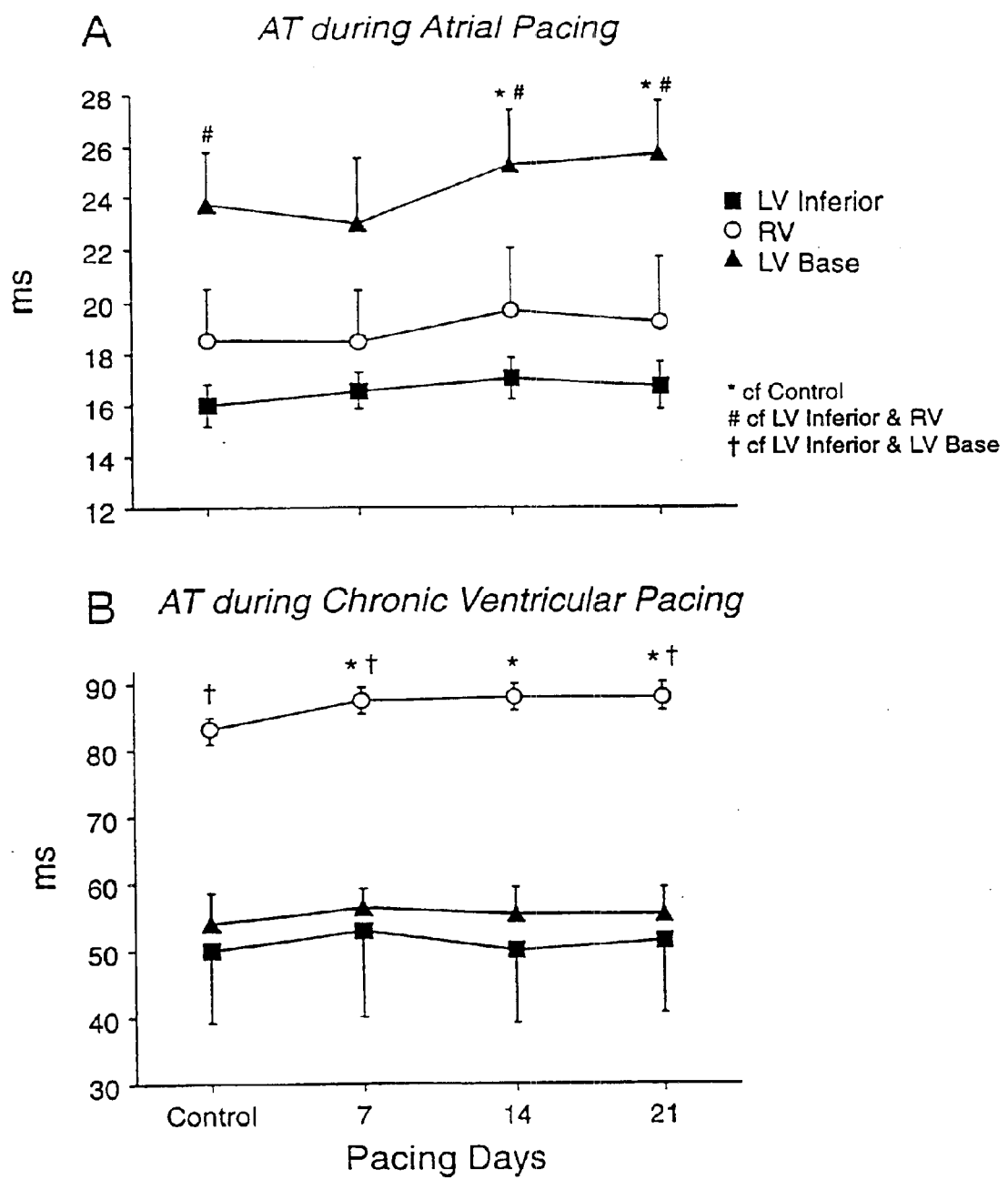
FIG. 2 is a graph showing activation times.

FIG. 2 is a graph showing activation times during control and on days 7, 14, and 21 during the 1 hour interludes of atrial pacing (Panel A) and during the ventricular pacing, itself (Panel B). In panel A for the two sites activated earliest (RV and LV inferior) there is no significant change in activation time. In contrast, for the site activated last (LV base) activation time prolongs during the protocol. Similarly, during ventricular pacing (Panel B) the two sites activated earliest (now LV inferior and LV base) show no change in activation time, while the area activated latest (RV) shows prolongation of activation time during the protocol. The symbol indicates P<0.05 cf control.

Figure 3:
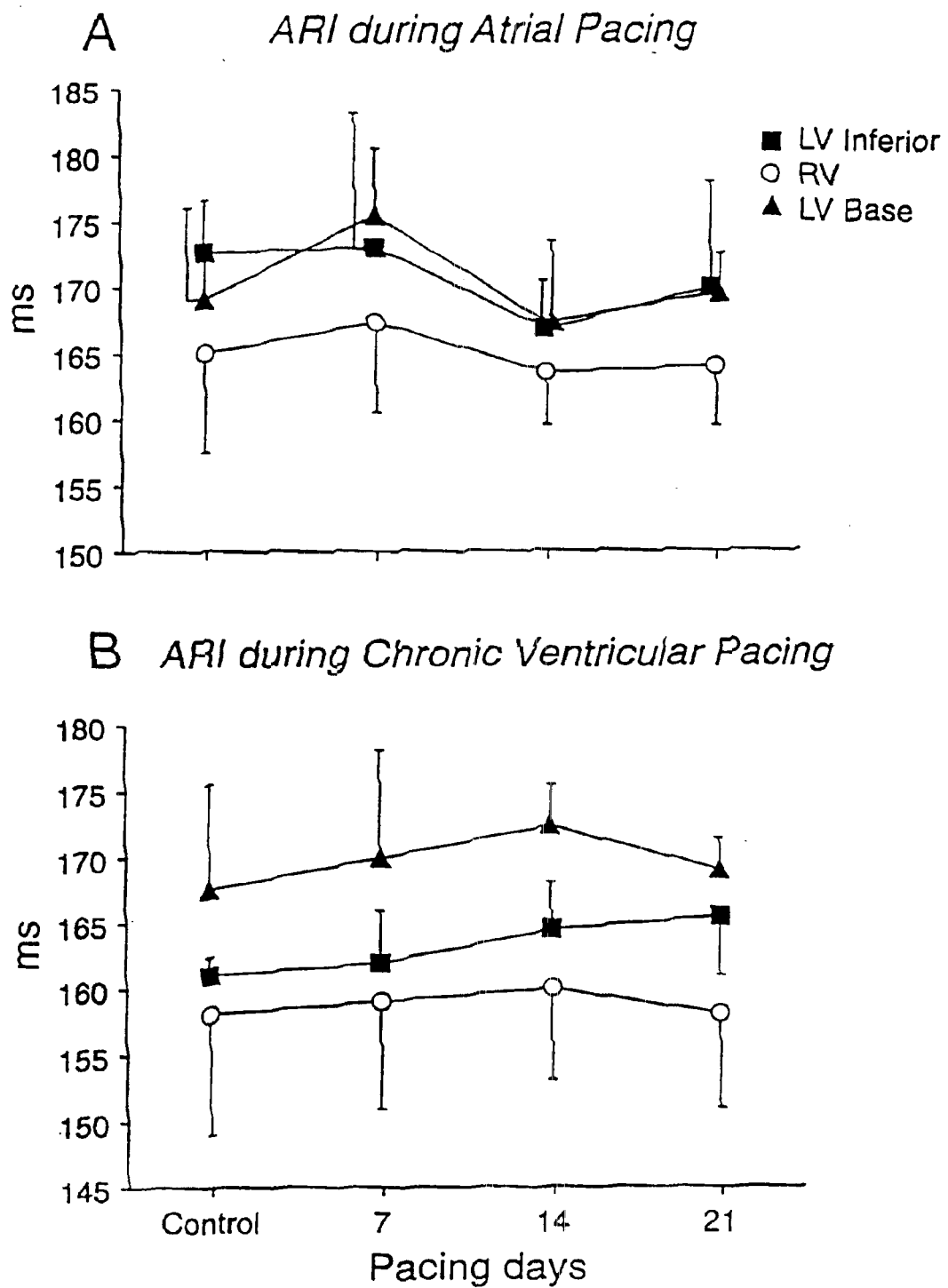
FIG. 3 is a graph showing activation-recovery times.

FIG. 3 is a graph showing activation-recovery intervals during control and on days 7, 14, and 21 during the 1 hour interludes of atrial pacing (Panel A) and during the ventricular pacing, itself (Panel B). In both panels there is no significant change in ARI at any of the sites studied.

Local electrogram measurements were done uniquely in Group II to define more clearly the changes occurring in activation and repolarization. As shown in FIGS. 2A (during atrial pacing) and 2B (during ventricular pacing) at sites of early activation during control no significant change occurs over 21 days. In contrast, at those sites that are activated late (LV base atrial pacing and anterior RV free wall during LV posterior pacing) there is a significant prolongation of activation time. During atrial (FIG. 3A) or ventricular (FIG. 3B) pacing, the Group II activation-recovery intervals did not change over the 21 day period. This result is similar to that seen for the QT interval (see Table 1).

Gap-junctional Remodeling
General Appearance of the Heart and Myocardium

The removed hearts from the paced animals appeared grossly normal, with minimal scarring and fibrosis limited exclusively to the pacemaker lead site. The left ventricular wall outside the immediate vicinity of the pacing site appeared normal, with no obvious edema, necrosis or scarring. Standard light microscopy revealed normal myocardial appearance and no differences between any of the myocardial layers in the paced or control groups.

Connexin43 Immunolabelling

These studies were done in Group I animals, in which the only cardiac instrumentation was the single, anterior left ventricular pacing lead.

Figure 4:
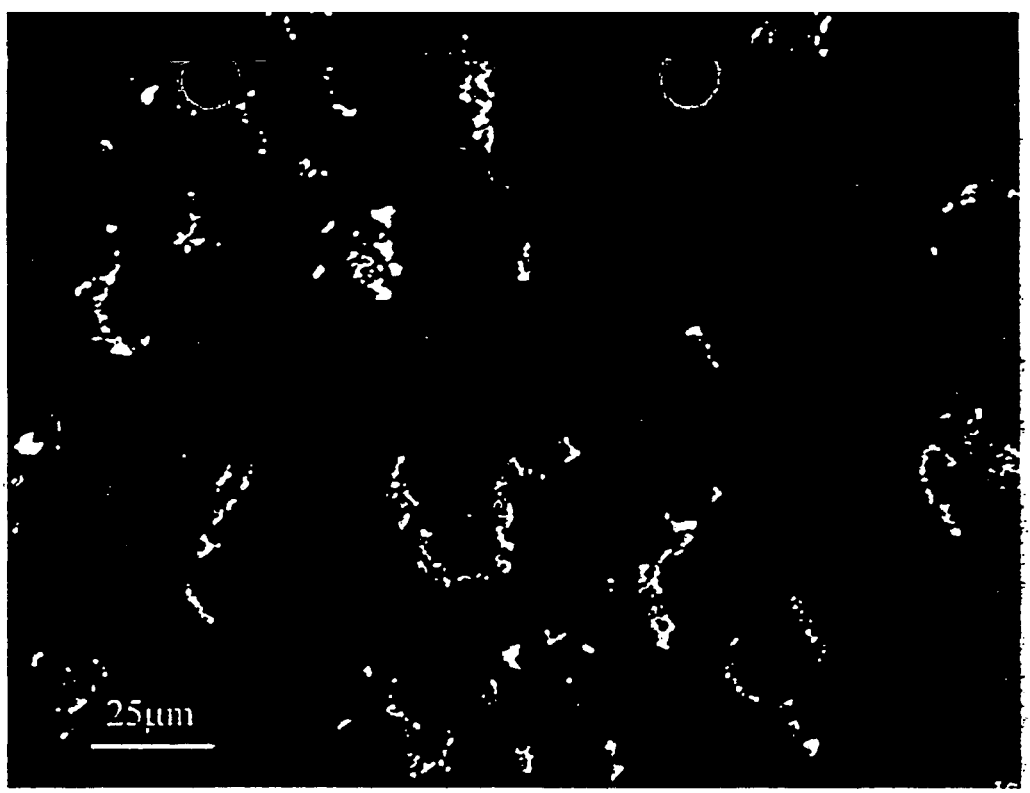
FIG. 4 comprises two confocal micrographs of the epimyocardial layer of the anterior left ventricular wall immunolabelled for connexin 43, from an unpaced control animal and a Group I animal paced for 21 days.
Figure 4:
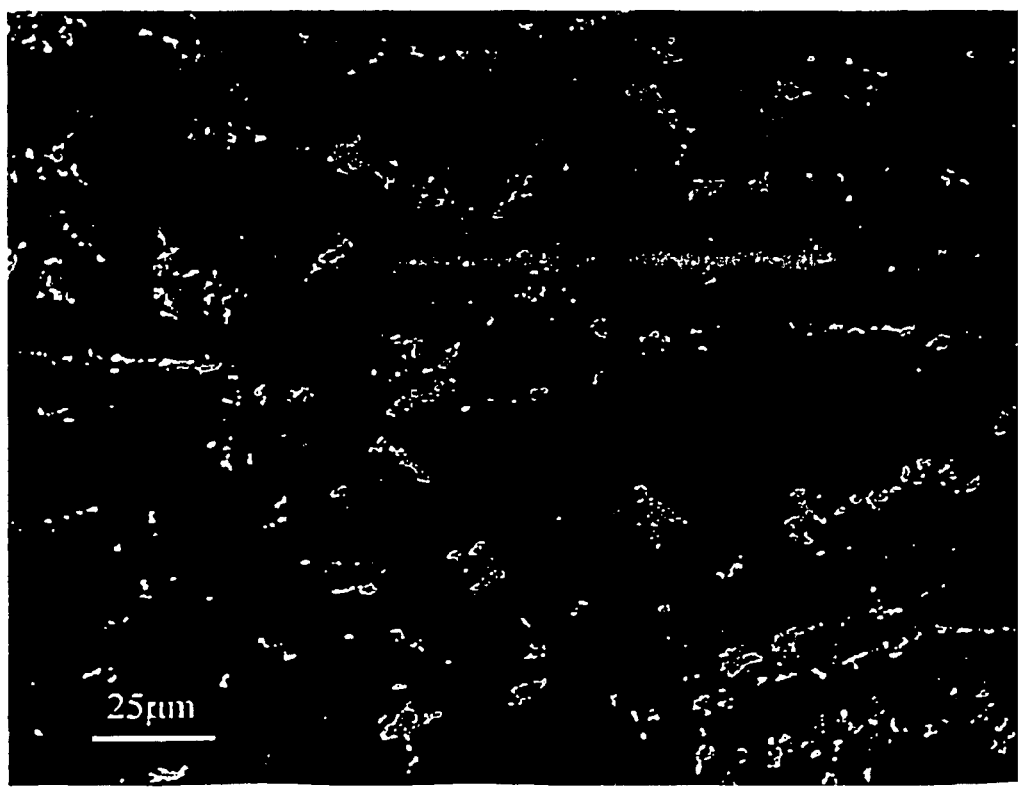

Control Animals: Optimization of the labeling protocols resulted in clear, consistent and uniform Cx43 labeling in all specimens, with a high signal/background ratio (FIG. 4). The pattern of gap junction distribution previously described in mammalian ventricular myocardium (23, 3, 5) was confirmed in the epicardial and endocardial layers of the control specimens. That is, with clusters of Cx43 gap junctions localized predominantly at the intercalated disks which are most prominent at the ends of abutting myocytes, and at the smaller disks which exist along the length of the cells, all orientated transverse to the long axis of the cell. Thus, with the myocardium sectioned parallel to the long axis (FIG. 4), the clusters appeared as transverse bands at intercellular abutments.

Paced Animals: By contrast with this normal pattern of distribution, the epimyocardial layer of the paced animals had, to a variable extent, an abnormal pattern of distribution of Cx43 Immunolabelling. The clusters of label tended to be strewn along the long axis of the cells, in longitudinally oriented arrays, with fewer discrete transversely orientated clusters. Representative images are shown in FIG. 4. To be able to summarize this finding for the entire groups of animals, a simple, arbitrary scoring system was used. A scale was devised with a score of 1 to 10 given to each individual sample depending upon the label distribution observed by a blinded operator. A score of "1" was given to an extreme distribution of connexin organization with labeling confined exclusively to the normal, transversely orientated clusters at cell abutments (FIG. 4A), and a score of "10" represented a distribution of labeling within longitudinal arrays along the myocyte, with markedly diminished labeling at the end-on abutments (FIG. 4B).

These semiquantitative data are summarized in Table 2. By contrast with the mid- and endocardial layers, the epicardium showed a clear alteration in label distribution I the paced dogs, compared with controls (FIG. 4). This is borne out by the mean scores for epicardium in Table 2 (control vs. paced, 3.0 vs. 7.0), although given the semiquantitative nature of these data, no attempt has been made to perform any statistical analysis.

TABLE 2

Subjective scores of distribution of Cx43 label in LV myocardial layers close to pacing site of paced and control dogs (Scale 1 to 10, where 1 = confined to transverse clusters, 10 = confined to longitudinal clusters)

| | EPI | MID | ENDO |
|---|---|---|---|
| CONTROL | | | |
| A | 2 | 5 | 2 |
| B | 4 | 5 | 5 |
| C | 2 | 6 | 2 |
| D | 2 | 4 | 4 |
| E | 5 | 4 | 2 |
| MEAN | 3.0 | 4.8 | 3.0 |
| PACED | | | |
| F | 8 | 4 | 3 |
| G | 6 | 3 | 2 |
| H | 8 | 3 | 3 |
| I | 4 | 4 | 2 |

TABLE 2-continued

Subjective scores of distribution of Cx43 label in LV myocardial layers close to pacing site of paced and control dogs (Scale 1 to 10, where 1 = confined to transverse clusters, 10 = confined to longitudinal clusters)

|      | EPI | MID | ENDO |
|------|-----|-----|------|
| J    | 9   | —   | 2    |
| MEAN | 7.0 | 3.5 | 2.4  |

FIG. 4 comprises two confocal micrographs which show the effects of chronic pacing on gap junctional remodeling of the epimyocardial layer of the anterior left ventricular wall (~1 cm from pacing site) immunolabelled for connexin43, from an unpaced control animal (Upper panel) and from a Group I animal paced for 21 days (Lower panel). Both micrographs are longitudinally sectioned myocardium, with the long axis of the constituent cells running horizontally. The transversely oriented clusters of connexin43 label confined to the intercalated disks at the transverse cell abutments in Upper Panel is characteristic of normal ventricular myocardium (Score 2 on the visual scale—see Results and Table 2). The Lower Panel is an illustrative example of the abnormal pattern of connexin43 label distribution, with a significant proportion of the label spread in clusters along the longitudinal borders of the myocytes (Score 8). In the memory setting the gap junctional staining, rather than concentrating at the ends of the myocytes is distributed along their lateral margins as well. This represents a significant redistribution of gap junctional location, and occurred in the absence of change is a reference protein (connexin 40, results not shown here)(see refs. 37, 38).

Quantitative western Blotting for Connexin43.

The values for relative Cx43 expression (normalized for actin loading) in the 3 myocardial layers in the paced and control samples, both near and distant to the pacing site are shown in Table 3. There were no significant differences in Cx43 expression between the tissue layers or between the samples from the anterior or posterior LV walls from control animals. Comparing the paced and control animals, however, there was a significant reduction in Cx43 expression in the epimyocardium of paced samples (61.7±18.4) compared to that of control samples (107±43.3; p=0.031). Cx43 expression showed a non-significant reduction in the endomyocardial layer adjacent to the pacing site compared with controls (82.8±30.2 vs 109.2±21.0; p=1.01). The posterior LV wall, distant from the pacing site, in the paced dogs showed no significant differences in Cx43 expression compared with controls.

TABLE 3

Results of quantitative Western blots of Cx43 expression LV myocardial layers of paced and control dogs.

|         | NEAR TO PACING SITE | | | DISTANT TO PACING SITE | | |
|---------|------|------|------|------|------|------|
|         | EPI  | MID  | ENDO | EPI  | MID  | ENDO |
| CONTROL |      |      |      |      |      |      |
| A       | 59.8 | 82.9 | 102.8 | 64.7 | 83.0 | 58.0 |
| B       | 100.0 | 96.2 | 136.7 | 86.1 | 123.3 | 108.4 |
| C       | 178.3 | 49.4 | 79.3 | 52.2 | 40.4 | 66.5 |
| D       | 101.8 | 99.7 | 118.0 | 99.9 | 80.2 | 102.0 |
| E       | 96.0 | 90.2 | 109.3 | 74.4 | 73.4 | 91.7 |

TABLE 3-continued

Results of quantitative Western blots of Cx43 expression LV myocardial layers of paced and control dogs.

|         | NEAR TO PACING SITE | | | DISTANT TO PACING SITE | | |
|---------|------|------|------|------|------|------|
|         | EPI  | MID  | ENDO | EPI  | MID  | ENDO |
| MEAN    | 107.2 | 83.7 | 109.2 | 75.5 | 80.0 | 85.3 |
| SD      | 43.3 | 20.2 | 21.0 | 18.5 | 29.5 | 22.1 |
| PACED   |      |      |      |      |      |      |
| F       | 85.3 | 133.5 | 96.1 | 103.6 | 51.8 | 99.8 |
| G       | 55.2 | 94.7 | 78.3 | 82.1 | 70.5 | 50.9 |
| H       | 74.3 | 64.5 | 89.4 | 97.7 | 72.6 | 97.6 |
| I       | 74.8 | 82.3 | 109.1 | 82.0 | 59.5 | 151.8 |
| J       | 65.3 | 130.7 | 119.7 | 100.1 | 94.6 | 128.1 |
| K       | 40.4 | 88.8 | 37.5 | 94.0 | 99.6 | 126.4 |
| L       | 36.7 | 113.3 | 49.1 | 92.7 | 98.4 | 114.6 |
| MEAN    | 61.7 | 101.1 | 82.8 | 93.2 | 78.1 | 109.8 |
| SD      | 16.4 | 25.7 | 30.2 | 8.4 | 19.5 | 31.9 |

Connexin40 Immunolabelling

Despite appropriate positive controls, there was no detectable Cx40 labeling of the ventricular myocytes from control or paced groups.

Electrode, Results, Pacing Modality

The following is a description of the electrode and of preliminary results using it, as well as the general modality of pacing to induce electrical, mechanical and gap junctional remodeling.

Figure 5:
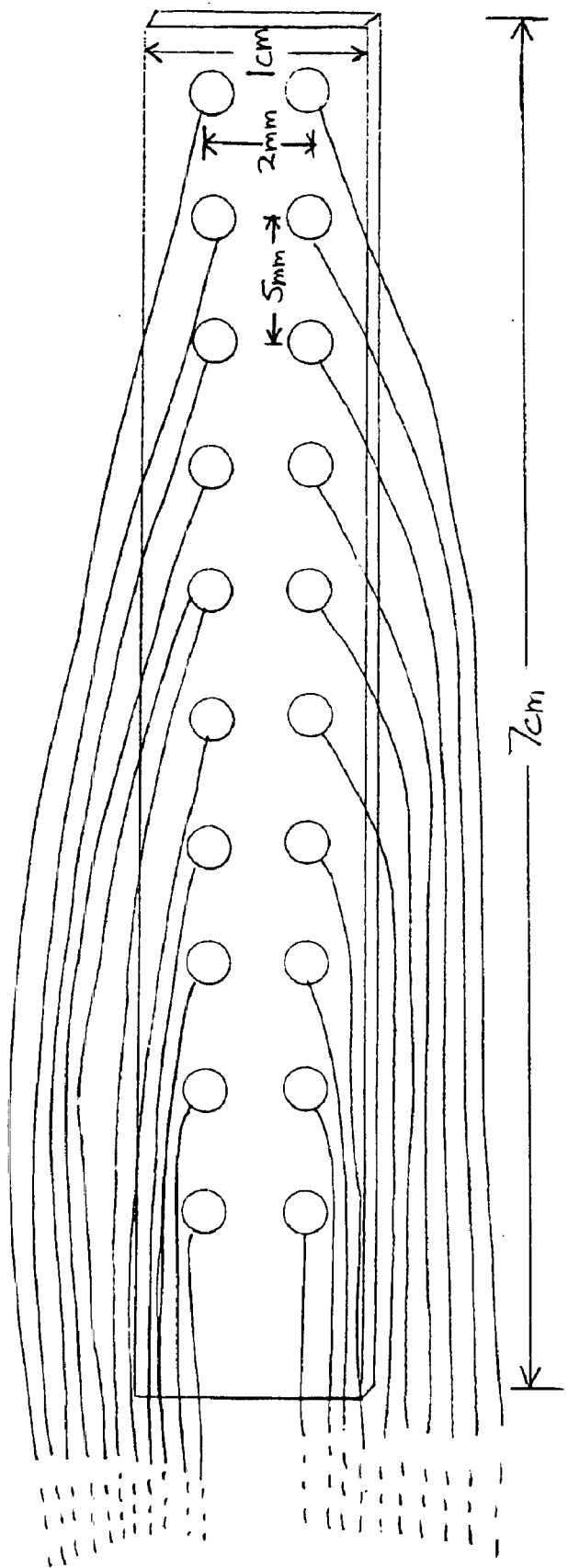
FIG. 5 is a drawing of an electrode array according to the invention.

The Electrode (FIG. 5)

As shown in FIG. 5, the electrode is a 7 cm×1 cm medical grade polyurethane (Biospan) strip having a plurality or multiplicity of 1.2 mm unalloyed platinum electrode pairs (each member of a pair spaced 2 mm from its mate) with the pairs spaced at 5 mm intervals. The electrodes are thus arranged in two columns with one electrode of the pair in one column, and the other electrode in the other column. The electrodes are linked or connected together as shown. Each electrode has an electrode wire. The wires are 30 gauge multi-stranded stainless steel covered with medical grade polyurethane. The array may be driven by any standard implantable pacemaker device, such that all electrodes or any subset of electrodes can contribute to a simultaneously activating wavefront. The signals from a standard pacemaker has certain signal characteristics (i.e. voltage, current, frequency) which has been shown to produce the desired results. Other signals can be used, provided they also produce the results desired, as described herein. The electrode strip can be sewn to the epicardial surface or, if re-arrayed on a transvenous catheter, placed into an epicardial vein via the coronary sinus or placed into the ventricles for endocardial activation. We have done experiments regarding the remodeling induced using both the entire array, or using point source stimulation from individual bipolar pairs.

Results:

The general indicator of remodeling that we use is a change in the electrocardiographic T wave. This is readily recordable from the body surface, requires no interventions in order to read it, and is recognized as the "gold standard" for cardiac memory (13, 17, 33), which is the specialized form of remodeling our pacing protocols induce.

Figure 6:
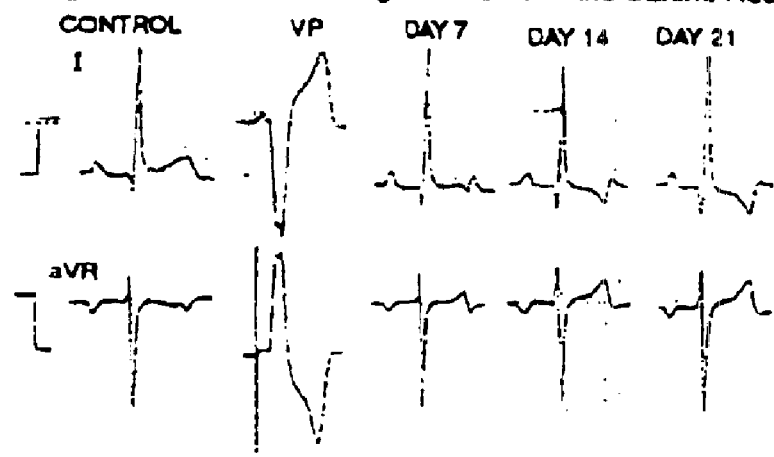
FIG. 6 shows electrocardiograms and vectrocardiograms of representative samples of effects of point source stimulation on accumulation of T wave changes.
Figure 6:
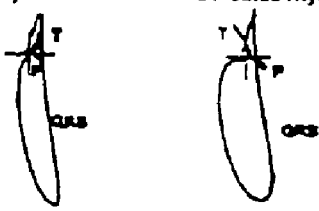
Figure 6:
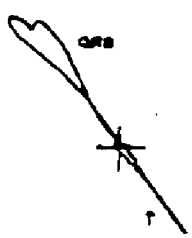
Figure 6:
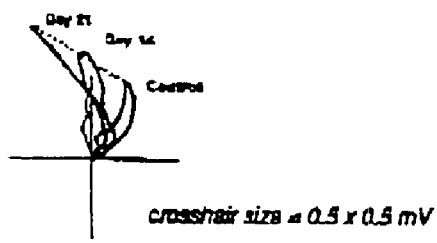

Point source stimulation:

FIG. 6 is a series of representative examples of effects of point source stimulation on accumulation of T wave changes on ECG and vectrocardiogram. Pacing was continued for 21 days and discontinued for an hour on days 7, 14, and 21. The T wave on ECG gradually assumes the ventor of the paced QRS complex. The T vector change is better appreciated on the vectorcardiographic records in the lower panels. Here, panel A is a control, B represents ventricular pacing, C is an enlargement of the T wave vectors at control and days 14 and 21 showing the shift in vector as seen during sinus rhythm, and panel D is the return to sinus rhythm on day 21 (see ref. 15).

As shown in FIG. 6, pacing of anesthetized dogs from a point source on the anterior left ventricle gives rise to an altered T wave on ECG that has the characteristics of memory (that is, with repeated stimulation the T wave change is increased and its decay from peak is more protracted with repeated periods of pacing) (15, 34).

Figure 7:
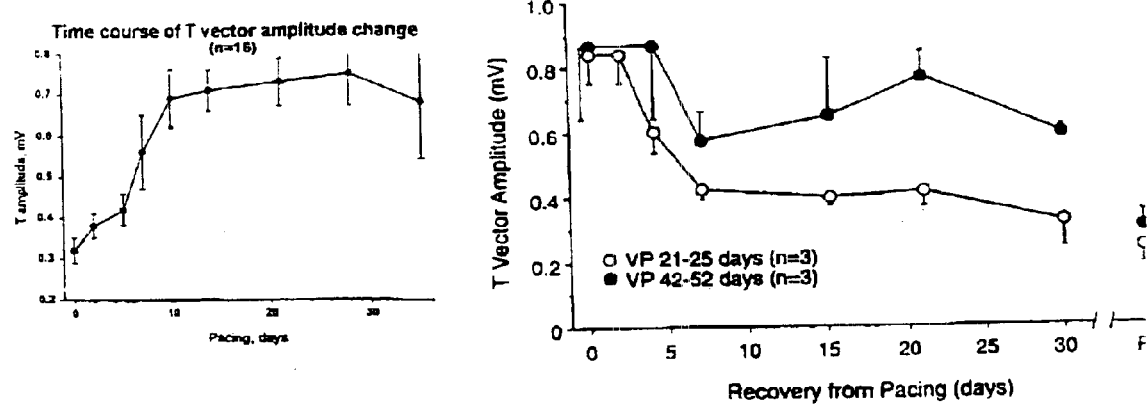
FIG. 7 comprise two graphs showing quantification of pacing-induced changes in sinus rhythm T vectoramplitude in animals, and the recovery of the T wave following cessation of pacing.

FIG. 7 is a series of two graphs showing quantification of pacing-induced changes in sinus rhythm T vector amplitude in 16 dogs during 35 days of pacing (left), demonstrating the major change to occur by 12 and the plateau fully evident by 22 days. On the right is recovery of the T wave following cessation of pacing. When pacing was 21–25 days in duration, recovery was rapid, and largely complete in a week. In contrast, following 42–52 days of pacing significant recovery had not occurred by one month (see ref. 15).

As shown in FIG. 7—left, the effect of long-term pacing of conscious dogs is to induce a peak change in the T wave at 21 days (15). This persists for variable periods thereafter, depending on the time the heart was initially paced (FIG. 7—right)(15, 34). These changes occur in the absence of significant alterations in ventricular hemodynamics or in myocardial flow (15) as demonstrated using standard hemodynamic and microsphere techniques. Moreover, there is no evidence of hypertrophy, based on measurements of cell capacitance (19).

TABLE 4

T Wave Displacement and Amplitude Change After 21 days Ventricular Pacing

|  | Control | 21 days (CM) |
|---|---|---|
| T displacement (mV) | 0.0 ± 0.0 | 0.74 ± 0.08 |
| T amplitude (mV) | 1.0 ± 0.2 | *1.6 ± 0.3 |

*-p < 0.05

As shown in Table 4, pacing of conscious dogs for 21 days via the posterolateral left ventricle induces the altered T wave on ECG characteristic of memory. The changes that occur in activation are shown in FIG. 8 (35).

Figure 8:
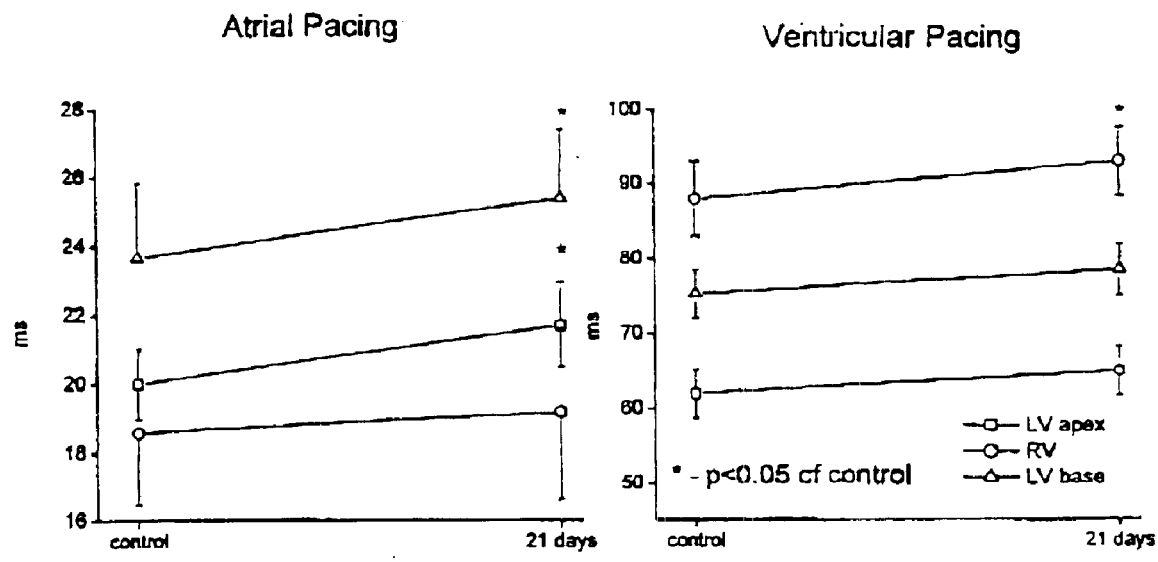
FIG. 8 is two graphs showing activation time measured from reference QRS to bipolar epicardial electrode sites at left ventricular apex, left ventricular base and right ventricle.

FIG. 8 is two graphs which show activation time measured from reference QRS to bipolar epicardial electrode sites at left ventricular (LV) apex, LV base and right ventricle (RV). Following 21 days of point source pacing from posterolateral LV, activation time is recorded during atrial pacing (left) to simulate sinus rhythm, or ventricuiar pacing (right). During atrial pacing, there is significant delay of activation to the latest sites activated (i.e. LV apex and base). During ventricular pacing, the delay in activation is again to the latest site, in this case, the RV.

During atrial pacing, to mimic sinus rhythm, there is a delay of activation to the sites activated last (i.e. left ventricular base and apex). In contrast, during ventricular pacing, the delay is to the site activated last in this situation, the lateral right ventricle. In other words, the normal physiological delays in activation expected as a result of altering the site of impulse initiation are not altered by the pacing to induce cardiac memory. Very importantly, in light of this, significant changes in repolarization and effective refractory period occur as shown in FIG. 9 (35, 36).

Figure 9:
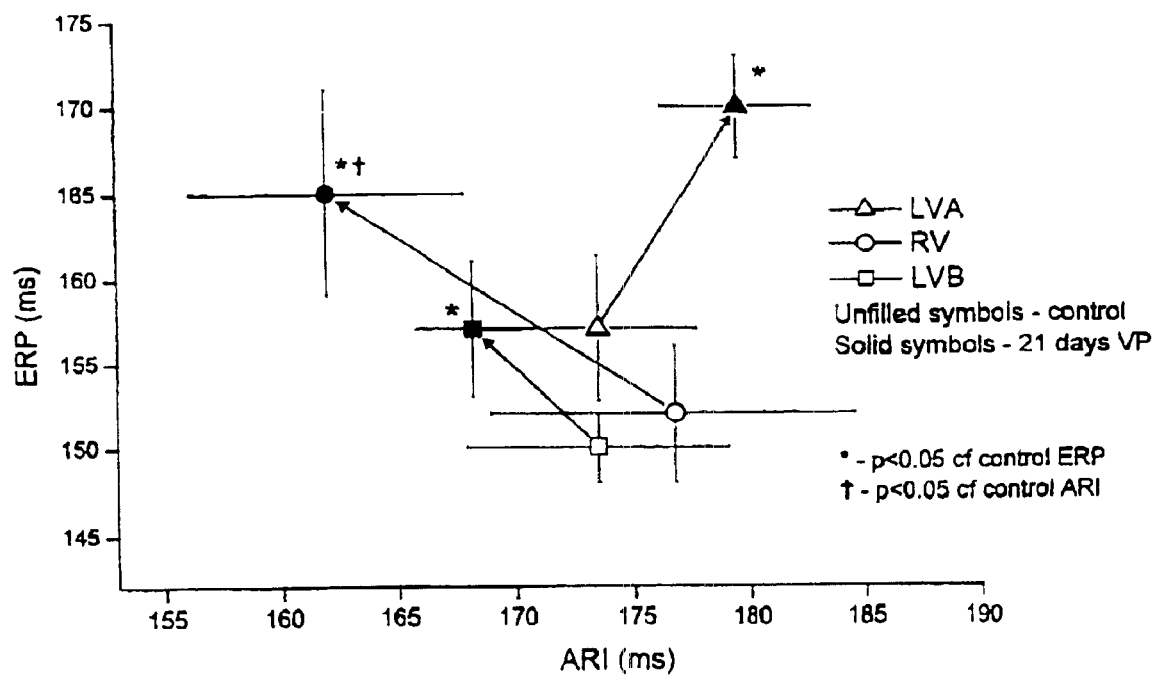
FIG. 9 is a graph showing changes in activation recovery intervals and effective refractory periods at the same sites and the same times as in FIG. 8.

FIG. 9 is a graph showing changes in activation-recovery intervals (ARI, reflecting duration of local repolarization) and effective refractory periods (ERP) at the same sites and the same times as in FIG. 8. Depending on site, the ARI (and with this, repolarization) may length or shorten. However, the ERP lengthens in every instance, demonstrating significant remodeling. At each site the ratio, ERP/ARI increases, indicating greater protection against the propagation of premature beats.

The most important aspect of FIG. 9 is that regardless of whether the duration of repolarization shortens or lengthens, as manifested in local recordings of activation-recovery intervals, the effective refractory period is prolonged. The net result is that there is greater protection at each site from the propagation of premature depolarizations than had occurred previously, in other words, a profound antiarrhythmic effect.

Figure 10:
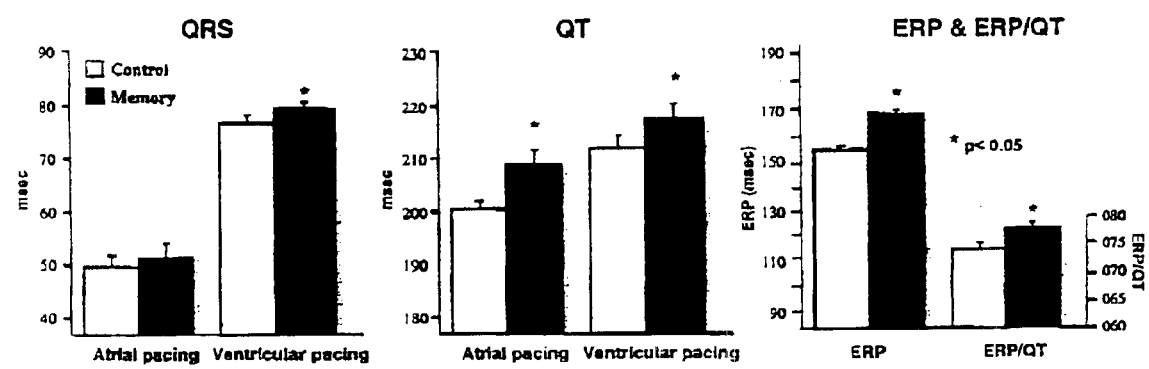
FIG. 10 is a series of three graphs showing the effect of 21 days of posterolateral LV pacing on the QRS duration, QT interval duration, effective refractory period (ERP) and ERP/QT ratio.

FIG. 10 is a series of three graphs showing the effect of 21 days of posterolateral LV pacing on the QRS duration, QT interval duration, effective refractory period (ERP) and ERP/QT ratio. Recordings are during control and after 21 days of pacing to induce cardiac memory. A slight prolongation in the QRS complex is seen during ventricular pacing, but not during atrial pacing. The QT interval, reflecting net repolarization measured from the body surface is increased during both types of pacing, and the ERP is prolonged significantly. Importantly, the ERP/QT ratio increases significantly indicating a greater protection against the propagation of premature beats.

A summary of the QRS and QT interval and effective refractory period changes as recorded on ECG is provided in FIG. 10. During ventricular, but not atrial, pacing there is a small but significant prolongation of the QRS complex. More importantly, during both atrial and ventricular pacing the QT interval is prolonged as is the effective refractory period during ventricular pacing. The most critical aspect of the prolongation in refractoriness and repolarization is that the change in the former is greater than the latter, such that the ratio, ERP/QT increases. The implication of all these results is that in settings where an arrhythmia is most likely to be propagated, the pacing intervention performed is most likely to prevent it from either expressing or sustaining itself.

Figure 11:
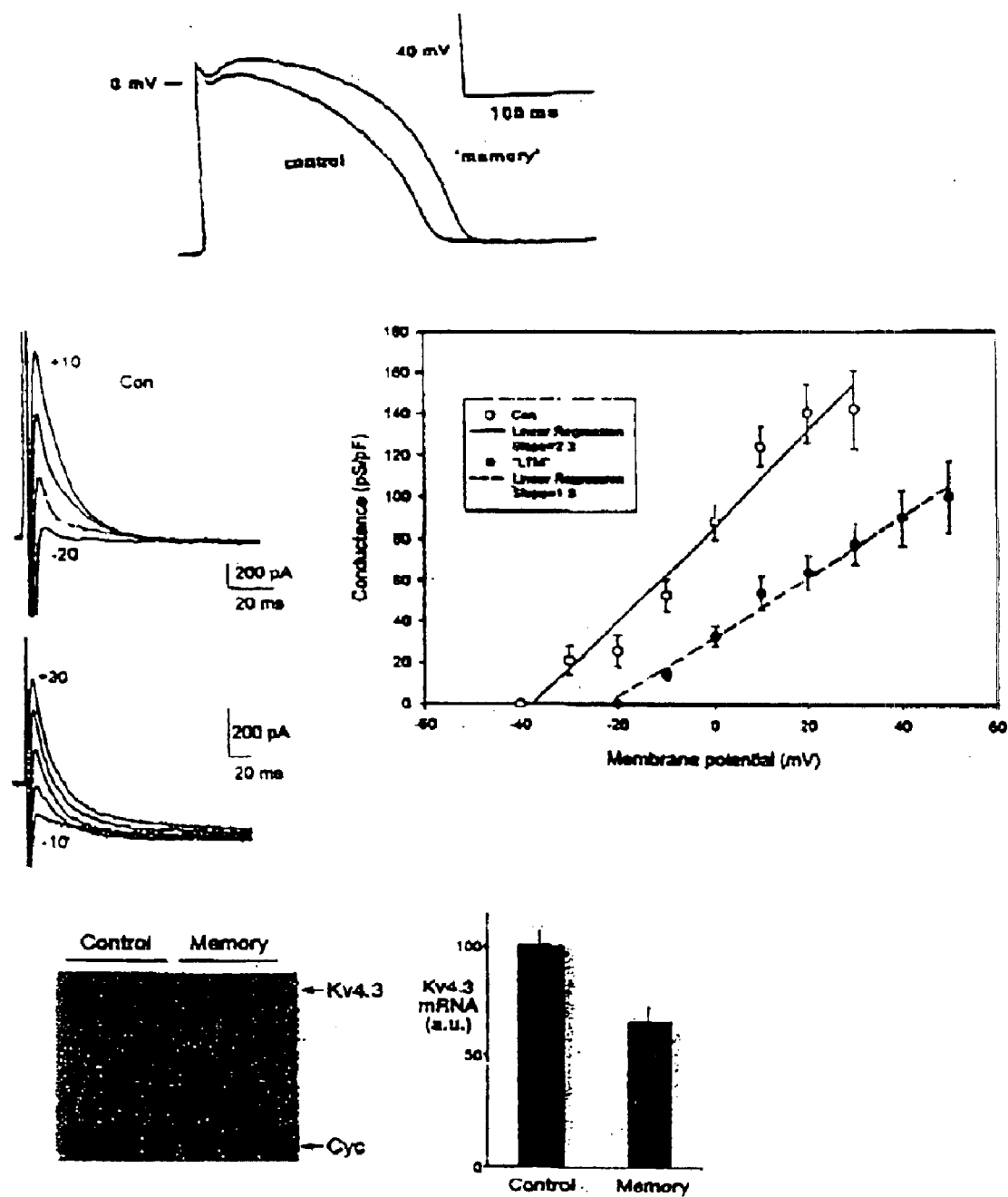
FIG. 11 is a series of graphs showing the effects of chronic pacing on action potential and ion channel remodeling.

FIG. 11 is a series of graphs showing the effects of chronic pacing on action potential and ion channel remodeling. The Upper panel, at a pacing cycle length of 650 msec, shows epicardial action potentials recorded from control and chronically paced dogs. The phase 1 notch (arrow) is more positive in the "memory" setting and that the plateau is higher and the action potential duration longer. This is entirely consistent with the QT interval changes reported in FIG. 9. The remaining panels deal with Ito, the ion channel responsible for the phase 1 notch. Middle panels on the left show currents recorded for Ito from single epicardial myocytes from a control (upper) and a memory (lower panel) animal. The current activates more negatively in control more negatively in control (around −20 mV) and een at +10 mV, has a far higher amplitude: On the right is a graph showing the mean results from all experiments looking at channel conductance. Over a wide range of voltages, a greater conductance, reflecting current, is seen in control than memory. The difference is about ⅓. Lower panels show Messenger RNA for Kv4.3, the genetic determinant of the Ito current in canine and human heart. On the left are results form 3 control and 3 memory animals, showing the reduction in Kv4.3 ("Cyc" refers to cyclophyllin, a reference gene). Results are quantified on the right, with Kv4.3 in memory being about ⅓ less than control, identical to the result seen with the current, itself, in the middle panels (see ref. 19).

FIG. 11 demonstrates changes in the action potential and its phase 1 notch; $I_{to}$, the ion current responsible for the action potential notch; and the messenger RNA for Kv4.3, understood to be the genetic determinant of $I_{to}$ in canine and human heart. In the upper panel the isolated cells show the same action potential prolongation described above for regional changes in activation-recovery intervals in the intact heart as well as a reduction in magnitude of the phase 1 notch. In the middle panel, $I_{to}$, which is responsible for the notch, decreases in magnitude by ⅓. In addition, and quite important, is that the activation voltage for the current moves from about −22 mV to −5 mV and the time constant for recovery from inactivation increases over 20-fold from a control of 27 ms. Finally, as shown in the lower panel, the message levels for Kv4.3 are reduced by ⅓. Hence, the entire trail of information is completely internally consistent, from action potential to ion current to molecular message (19) and indicates that ion channel remodeling has occurred.

Figure 12:
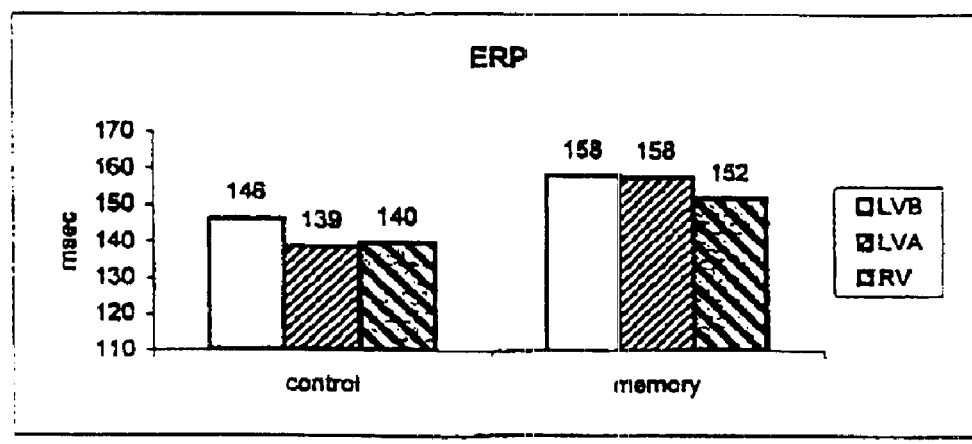
FIG. 12 show effective refractory period (ERP) measurements made following two one hour periods of left ventricular anteroseptal pacing using the array in three anesthetized dogs.

FIG. 4 demonstrates gap junctional remodeling induced by 21 days of pacing. The upper panel is a control, and the lower panel is the same region from an animal that was paced. The entire gap junctional distribution has changed, with lateralization clearly visualized. Measurements of epi-myocardial connexin43 expression using quantitative Western blotting revealed a reduction from a control of 107±43 to 62±18 (P<0.05, n=12) within a 3 cm radius of the pacemaker, following 21 days of VVO pacing (37, 38). Array stimulation:

FIG. 12 shows effective refractory period (ERP) measurements made following two one hour periods of left ventricular anteroseptal pacing using the array in three anesthetized dogs. The results show that there is an 8–12% increase in the ERP (upper), with significant prolongation demonstrable at each of the three reference sites measured (lower).

FIG. 12 demonstrates the changes seen in effective refractory period using the electrode array in the anteroseptal position in 3 anesthetized dogs paced for two 60 minute periods with a 30 minute respite of atrial pacing after each hour of ventricular pacing. Even after these relatively brief pacing periods there is a significant prolongation in effective refractory period at each site (8% each at left ventricular base and right ventricle and 12% at left ventricular apex). In other words, at three widely dispersed sites in the heart, refractoriness is prolonged.

REFERENCES

1. Page, E. Cardiac Gap Junctions. In: *The Heart and Cardiovascular System*. H. A. Fozzard, E. Haber, R. B. Jennings, A. M. Katz, and H. E. Morgan (eds). New York: Raven Press Ltd. 1992; 1003–1048.

2. Spach M S, Miller W T III, Dolber P C, Kootsey J M, Sommer J R, Mosher C E Jr. The functional role of structural complexities in the propagation of depolarization in the atrium of the dog. Cardiac conduction distrubances due to discontinuities of effective axial resistivity. *Circ Res.* 1982; 50:175–191.

3. Smith J H, Green C R, Peters N S, Rothery S, Severs N J Altered patterns of gap junction distribution in ischemic heart disease. An immunohistochemical study of human myocardium using laser scanning confocal microscopy. *Am J Pathol.* 1991; 139:801–821.

4. Luke R A, Saffitz J E. Remodeling of ventricular conduction pathways in healed canine infarct border zones. *J Clin Invest.* 1991;87:1594–1602.

5. Peters N S, Green C R, Poole-Wilson P A, Severs N J. Reduced content of connexin43 gap junctions in ventricular myocardium from hypertrophied and ischaemic human hearts. *Circulation.* 1993;88:864–875.

6. Campos De Carvalho A C, Tanowitz H B, Wittner M. Dermietzel R, Roy C, Hertzberg E L, Spray D C. Gap junction distribution is altered between-cardiac myocytes infected with *Trypanosoma cruzi*. *Circ Res.* 1992;70:733–742.

7. Bastide B, Neyses L, Ganten D, Paul M, Willecke K, Traub O. Gap junction protein connexin40 is preferentially expressed in vascular endothelium and conductive bundles of rat myocardium and is increased under hypertensive conditions. *Circ Res.* 1993;73:1138–1149.

8. Fast V G, Darrow B J, Saffitz J E, Kleber A G. Anisotropic activation spread in heart cell monolayers assessed by high-resolution optical mapping. Role of tissue discontinuities. *Circ Res.* 1996;79:115–127.

9. Guerrero-P-A; Schuessler-R-B; Davis-L-M; Beyer-E-C; Johnson-C-M; Yamada-K-A; Saffits-J-E: Slow ventricular conduction in mice heterozygous for a connexin43 null mutation. Journal of Clinical Investigation 1997;99(8): 1991–1998.

10. Peters N S, Severs N J, Coromilas J, Wit A L. Disturbed connexin43 gap junctional distribution correlates with the location of reentrant circuits in the epicardial border zone of healing canine infarcts that cause ventricular tachycardia. *Circulation.* 1997 95;988–996.

11. Wijffels M C E F, Kirchhof C J H J, Dorland R, Allessie M A: Atrial fibrillation begets atrial fibrillation. Circulation 1995;92: 1954–1968.

12. Kajstura-J; Zhang-X; Liu-Y; Szoke-E; Cheng-W; Olivetti-G; Hintze-T-H; Anversa-P: The cellular basis of pacing-induced dilated cardiomyopathy: Myocyte cell loss and myocyte cellular reactive hypertrophy. Circulation 1995; 92(8): 2306–2317.

13. Rosenbaum M B, Blanco H H, Elizari M V, Lazzari J O, Davidenko J M: Electronic modulation of the T wave and cardia memory. Am J Cartel 1982;50:2130222.

14. Chattered K, Harris A, Davies G, Leatham A: Electrocardiographic changes subsequent to artificial ventricular depolarization. Br Heart J 1969;31:770–779.

15. Shvilkin A, Danilo P, Jr. Wang J, Burkhoff D, Anyukhovsky E P, Sosunov E A, Hara M. Rosen M R. The evolution and resolution of long-term cardiac memory. Circulation 1998;97:1810–1817.

16. del Balzo U, Rosen M R: T wave changes persisting after ventricular pacing in canine heart are altered by 4-aminopyridine but not by lidocaine. Circulation 1992;85: 1464–1472.

17. Katz A M: T wave "Memory": Possible causal relationship to stress-induced changes in cardiac ion channels? J Cardiovasc Electrophysiol 1992;3:150–159.

18. Tan, R C; Joyner, R W: Electronic influences on action potentials from isolated ventricular cells. Circ Res: 1990:67: 1071–1081)

19. Yu H, McKinnon D, Dixon J E, Gao J, Wymore R, Cohen I S, Danilo, P Jr., Shvilkin A, Anyukhovsky E P, Sosunov E A, Hara M, Rosen M R: The transient outward current, $I_{to1}$, is altered in cardiac memory. Circulation, 1999; 99:1898–1905.

20. Anyukhovsky E P, Sosunov E A, Feinmark S J, et al: Effects of quinidine on repolarization in canine epicardium, midmyocardium, and endocardium: II. In vivo study. Circulation 1997;96:4019–4026.

21. Anyukhovsky E P, Sosunov E A, Gainullin R Z, Rosen M R. The controversial M cell J Cardiovasc Electrophysiol, in press.

22. Yeh-H-I; Dupont-E; Coppen-S; Rothery-S; Severs-N-J: Gap junction localization and connexin expression in cytochemically identified endothelial cells of arterial tissue. Journal of Histochemistry and Cytochemistry 1997; 45(4): 539–550.

23. Hoyt R H, Cohen M L, Saffitz J E. Distribution and three-dimensional structure of intercellular junctions in canine myocardium. Circ. Res. 1989;64:563–574.

24. Peters N S, Wit A L. Myocardial architecture and ventricular arrhythmogenesis. Circulation 1998;97: 1746–1754.

25. Spach M S, Dolber P C. The relation between discontinuous propagation in anisotropic cardiac muscle and the "vulnerable period" of reentry. In: Cardiac Electrophysiology and Arrhythmias D. P. Zipes and J. Jalife (eds). Grune and Stratton, Orlando. 1985;241–252.

26. Wit A L, Janse M J: Basic mechanisms of arrhythmias, in *The Ventricular Arrhythmias of Ischemia and Infarction*. New York, Futura, 1992, pp. 1–160.

27. Lesh M D, Pring M, Spear J F: Cellular uncoupling can unmask dispersion of action potential duration in ventricular myocardium. Circ. Res. 1989;65:1426–1440.

28. Elvan A. Wylie K, Zipes D P: Pacing-induced chronic atrial fibrillation impairs sinus node function in dogs. Electrophysiological remodeling. Circulation 1996;94:2953–60.

29. Yue-L; Feng-J; Gaspo-R; Li-G-R; Wang-Z; Nattel-S: Ionic remodeling underlying action potential changes in a canine model of atrial fibrillation. Circulation Research 1997;81(4): 512–525.

30. Quan W, Rudy Y: unidirectional block and reentry of cardiac excitation: a model study. Circ. Res. 1990;66:367–382.

31. Van-Der-Velden-Huub-M-W; Van-Kempen-Marjan-J-A; Wijffels-Maurits-C-E-F; Van-Zijverden-Maaike; Groenewegen-W-Antoinette; Allessie-Maurits-A; Jongsma-Habo-J: Altered pattern of connexin40 distribution in persistent atrial fibrillation in the goat. Journal-of-Cardiovascular-Electrophysiology. June, 1998;9(6) 595–607.

32. Patel P, Jones D G, Hadjinicolou L, Glenville B, Stanbridge R, Severs N J, Peters N S. Changes in human atrial connexin expression in arterial fibrillation and ischemic heart disease. Circulation 1997; 96(8) : 1–17.

What is claimed is:

1. A method of treating a heart to remodel gap junctions to alter contractile patterns and to prevent arrhythmias, comprising contacting linked multiple electrode pairs to an epicardial a surface of the heart, and connecting the electrode pairs to a pacemaker to apply periodic pacing level electrical signals to the surface through said electrode pairs, said signals being applied for a sufficient time and having characteristics sufficient to remodel gap junctions in the heart.

2. The method according to claim 1, wherein the step of contacting comprises contacting a strip electrode material having linked multiple electrode pairs mounted thereon.

3. The method according to claim 2, wherein the strip electrode material comprises a strip of medical grade polyurethane.

4. The method according to claim 3, wherein the strip is about 7 cm×1 cm in dimension.

5. The method according to claim 1, wherein the step of contacting comprises contacting linked multiple electrode pairs to an epicardial surface of the heart, wherein the linked multiple electrode pairs are arranged in two columns with one electrode in each pair in one column, and the other electrode in each pair in the other column.

6. The method accord ing to claim 5, wherein each electrode in the electrode pair is about 2 mm from each other, and wherein each electrode pair is about 5 mm from its closest electrode pair.

7. The method according to claim 1, wherein the electrodes comprise platinum.

8. The method according to claim 7, wherein the electrodes consist essentially of unalloyed platinum.

9. The method according to claim 1, wherein the step of contacting comprises sewing a substrate strip containing linked multiple electrode pairs to an epicardial surface of the heart.

10. The method according to claim 1, wherein the step of contacting comprises locating a transvenous catheter containing linked multiple electrode pairs into an epicardial vein.

11. The method according to claim 1, wherein the step of contacting comprises placing electrodes into heart ventricles for endocardial activation.

12. A device for treating a heart to obtain gap junctional remodeling to alter contractile patterns and to prevent arrhythmias, comprising a substrate having linked multiple electrode pairs for contacting a surface of the heart and a pacemaker for delivering periodic pacing level electrical signals to the surface through said electrode pairs, to remodel gap junctions in the heart.

13. The device according to claim 12, further comprising a strip of electrode material having mounted thereon the linked multiple electrode pairs.

14. The device according to claim 13, wherein the electrode material comprises medical grade polyurethane.

15. The device according to claim 12, wherein the electrode pairs are arranged in two columns with one electrode in each pair in one column, and the other electrode in each pair in the other column.

16. The device according to claim 15, wherein one electrode in the pair is about 2 mm from the other electrode in the pair, and wherein each electrode pair is about 5 mm from its closest elect rode pair.

17. The device according to claim 12, wherein the electrodes are comprised of platinum.

18. The device according to claim 17, wherein the electrodes consist essentially of unalloyed platinum.

19. The device according to claim 12, wherein each electrode is connected to an insulated stainless steel wire.

20. A method of treating a heart to alter the effective refractory period to alter contractile patterns and to prevent arrhythmias, comprising contacting linked multiple electrode pairs to a surface of the heart, and connecting the electrode pairs to a pacemaker to apply periodic pacing level electrical signals to the surface, said signals being applied for a sufficient time and having characteristics sufficient to alter the effective refractory period of the heart.

21. The method according to claim 20, wherein the step of contacting comprises contacting a strip electrode material having linked multiple electrode pairs mounted thereon.

22. The method according to claim 21, wherein the strip electrode material comprises a strip of medical grade polyurethane.

23. The method according to claim 22, wherein the strip is about 7 cm×1 cm in dimension.

24. The method according to claim 20, wherein the step of contacting comprises contacting linked multiple electrode pairs to an epicardial surface of the heart, wherein the linked multiple electrode pairs are arranged in two columns with one electrode in each pair in one column, and the other electrode in each pair in the other column.

25. The method according to claim 24, wherein each electrode in the electrode pair is about 2 mm from each other, and wherein each electrode pair is about 5 mm from its closest electrode pair.

26. The method according to claim 20, wherein the electrodes comprise platinum.

27. The method according to claim 26, wherein the electrodes consist essentially of unalloyed platinum.

28. The method according to claim 20, wherein the step of contacting comprises sewing a substrate strip containing linked multiple electrode pairs to an epicardial surface of the heart.

29. The method according to claim 20, wherein the step of contacting comprises locating, a transvenous catheter containing linked multiple electrode pairs into an epicardial vein.

30. The method according to claim 20, wherein the step of contacting comprises placing electrodes into heart ventricles for endocardial activation.

31. A device for treating a heart to alter the effective refractory period to alter contractile patterns and to prevent arrhythmias, comprising a substrate having linked multiple electrode pairs for contacting a surface of the heart and a pacemaker for delivering periodic pacing level electrical signals to the surface through said electrode pairs, to alter the effective refractory period in the heart.

32. The device according, to claim 31, further comprising a strip of electrode material having mounted thereon the linked multiple electrode pairs.

33. The device according to claim 32, wherein the electrode material comprises medical grade polyurethane.

34. The device according to claim 31, wherein the at least two electrode pairs are arranged in two columns with one electrode in each pair in one column, and the other electrode in each pair in the other column.

35. The device according to claim 34, wherein one electrode in the pair is about 2 mm from the other electrode in the pair, and wherein each electrode pair is about 5 mm from its closest electrode pair.

36. The device according to claim 31, wherein the electrodes are comprised of platinum.

37. The device according to claim 36, wherein the electrodes consist essentially of unalloyed platinum.

38. The device according to claim 31, wherein each electrode is connected to an insulated stainless steel wire.

39. A method of treating a heart to induce ion channel remodeling to alter contractile patterns and to prevent arrhythmias, comprising contacting linked multiple electrode pairs to a surface of the heart, and connecting the electrode pairs to a pacemaker to apply pacing level electrical signals to the surface, said signals being applied for a sufficient time and having characteristics sufficient to induce ion channel remodeling in the heart.

40. The method according to claim 39, wherein the step of contacting comprises contacting a strip electrode material having linked multiple electrode pairs mounted thereon.

41. The method according to claim 40, wherein the strip electrode material comprises a strip of medical grade polyurethane.

42. The method according to claim 41, wherein the strip is about 7 cm×1 cm in dimension.

43. The method according to claim 39, wherein the step of contacting comprises contacting linked multiple electrode pairs to an epicardial surface of a heart, wherein the linked multiple electrode pairs are arranged in two columns with one electrode in each pair in one column, and the other electrode in each pair in the other column.

44. The method according to claim 43, wherein each electrode in the electrode pair is about 2 mm from each other, and wherein each electrode pair is about 5 mm from its closest electrode pair.

45. The method according to claim 39, wherein the electrodes comprise platinum.

46. The method according to claim 45, wherein the electrodes consist essentially of unalloyed platinum.

47. The method according to claim 39, wherein the step of contacting comprises sewing a substrate strip containing linked multiple electrode pairs to an epicardial surface of the heart.

48. The method according to claim 39, wherein the step of contacting comprises locating a transvenous catheter containing linked multiple electrode pairs into an epicardial vein.

49. The method according to claim 39, wherein the step of contacting comprises placing electrodes into heart ventricles for endocardial activation.

50. A device for treating a heart to induce ion channel remodeling to alter contractile patterns and to prevent arrhythmias, comprising a substrate having linked multiple electrode pairs for contacting a surface of the heart and a pacing level for delivering periodic pacemaker electrical signals to the surface through said electrode pairs, to induce ion channel remodeling in the heart.

51. The device according to claim 50, further comprising a strip of electrode material having mounted thereon the linked multiple electrode pairs.

52. The device according to claim 51, wherein the electrode material comprises medical grade polyurethane.

53. The device according to claim 50, wherein the electrode pairs are arranged in two columns with one electrode in each pair in one column, and the other electrode in each pair in the other column.

54. The device according to claim 53, wherein one electrode in the pair is about 2 mm from the other electrode in the pair, and wherein each electrode pair is about 5 mm from its closest electrode pair.

55. The device according to claim 50, wherein the electrodes are comprised of platinum.

56. The device according to claim 55, wherein the electrodes consist essentially of unalloyed platinum.

57. The device according to claim 50, wherein each electrode is connected to an insulated stainless steel wire.

58. A device for treating a heart to obtain gap junctional remodeling to alter contractile patterns and to prevent arrhythmias, comprising a substrate having linked multiple electrode pairs for contacting a surface of the heart and for delivering periodic pacing level signals to the surface through said electrode pairs, to remodel gap junctions in the heart, wherein the electrode pairs are arranged in two columns with one electrode in each pair in one column, and the other electrode in each pair in the other column.

59. A device for treating a heart to alter the effective refractory period to alter contractile patterns and to prevent arrhythmias comprising a substrate having linked multiple electrode pairs for contacting a surface of the heart and for delivering periodic pacing level signals to the surface through said electrode pairs, to alter the effective refractory period in the heart, wherein the electrode pairs are arranged in two columns with one electrode in each pair in one column, and the other electrode in each pair in the other column.

60. A device for treating a heart to induce ion channel remodeling to alter contractile patterns and to prevent arrhythmias comprising a substrate having linked multiple electrode pairs for contacting a surface of the heart and for delivering periodic pacing level signals to the surface through said electrode pairs, to induce ion channel remodeling in the heart, wherein the electrode pairs are arranged in two columns with one electrode in each pair in one column, and the other electrode in each pair in the other column.

* * * * *

UNITED STATES PATENT AND TRADEMARK OFFICE
CERTIFICATE OF CORRECTION

| | | |
|---|---|---|
| PATENT NO. | : 6,868,287 B1 | Page 1 of 1 |
| APPLICATION NO. | : 09/505458 | |
| DATED | : March 15, 2005 | |
| INVENTOR(S) | : Michael R. Rosen et al. | |

It is certified that error appears in the above-identified patent and that said Letters Patent is hereby corrected as shown below:

Column 1, Line 3; beneath the title, please insert:

--FEDERAL FUNDING--

--This invention was made with government support under grant/contract number HL-53956 awarded by USPHS – NHLBI. The government has certain rights to the invention.--

Signed and Sealed this

Fifteenth Day of July, 2008

JON W. DUDAS
*Director of the United States Patent and Trademark Office*